(12) United States Patent
Deng et al.

(10) Patent No.: US 12,178,943 B2
(45) Date of Patent: Dec. 31, 2024

(54) COMPOSITIONS AND MATERIALS FOR REGENERATION OF SKELETAL MUSCLE

(71) Applicant: Purdue Research Foundation, West Lafayette, IN (US)

(72) Inventors: Meng Deng, West Lafayette, IN (US); Naagarajan Narayanan, Boulder, CO (US); Shihuan Kuang, West Lafayette, IN (US)

(73) Assignee: Purdue Research Foundation

( * ) Notice: Subject to any disclaimer, the term of this patent is extended or adjusted under 35 U.S.C. 154(b) by 206 days.

(21) Appl. No.: 17/184,231

(22) Filed: Feb. 24, 2021

(65) Prior Publication Data

US 2021/0330870 A1    Oct. 28, 2021

Related U.S. Application Data

(60) Provisional application No. 63/016,386, filed on Apr. 28, 2020.

(51) Int. Cl.
*A61L 31/14* (2006.01)
*C07K 14/47* (2006.01)
*C12N 5/079* (2010.01)

(52) U.S. Cl.
CPC .......... *A61L 31/145* (2013.01); *C07K 14/47* (2013.01); *C12N 5/0618* (2013.01)

(58) Field of Classification Search
None
See application file for complete search history.

(56) References Cited

U.S. PATENT DOCUMENTS

2015/0125952 A1* 5/2015 Kim ............... C12N 5/0696 435/396
2019/0117782 A1* 4/2019 Schaffer ............ A61K 38/1833

FOREIGN PATENT DOCUMENTS

WO    WO-2018213375 A1 * 11/2018 ............ A61K 35/34
WO    WO-2020168327 A1 *  8/2020 ........... A61B 5/4851

OTHER PUBLICATIONS

Willis, C. M., Nicaise, A. M., Peruzzotti-Jametti, L., & Pluchino, S. (2019). The neural stem cell secretome and its role in brain repair. Brain research, 1729, 146615. (Year: 2019).*
Kim, J. H., Kim, I., Seol, Y. J., Ko, I. K., Yoo, J. J., Atala, A., & Lee, S. J. (2020). Neural cell integration into 3D bioprinted skeletal muscle constructs accelerates restoration of muscle function. Nature communications, 11(1), 1025. (Year: 2020).*
Ostrovidov, S., Ahadian, S., Ramon-Azcon, J., Hosseini, V., Fujie, T., Parthiban, S. P., . . . & Khademhosseini, A. (2017). Three-dimensional co-culture of C2C12/PC12 cells improves skeletal muscle tissue formation and function. Journal of tissue engineering and regenerative medicine, 11(2), 582-595. (Year: 2017).*
Aregueta-Robles, U. A., Martens, P. J., Poole-Warren, L. A., & Green, R. A. (2019). Tissue engineered hydrogels supporting 3D neural networks. Acta Biomaterialia, 95, 269-284. (Year: 2019).*
Castilho, M., van Mil, A., Maher, M., Metz, C. H., Hochleitner, G., Groll, J., . . . & Malda, J. (2018). Melt electrowriting allows tailored microstructural and mechanical design of scaffolds to advance functional human myocardial tissue formation. Advanced Functional Materials, 28(40), 1803151. (Year: 2018).*
Morimoto, Y., Kato-Negishi, M., Onoe, H., & Takeuchi, S. (2013). Three-dimensional neuron-muscle constructs with neuromuscular junctions. Biomaterials, 34(37), 9413-9419. (Year: 2013).*
Westerink, R. H. S., & Ewing, A. G. (2008). The PC12 cell as model for neurosecretion. Acta Physiologica, 192(2), 273-285. (Year: 2008).*
Townley, R. A., Boeve, B. F., & Benarroch, E. E. (2018). Progranulin: functions and neurologic correlations. Neurology, 90(3), 118-125. (Year: 2018).*
Pratt SJP, Valencia AP, Le GK, Shah SB, Lovering RM. Pre- and postsynaptic changes in the neuromuscular junction in dystrophic mice. Front Physiol. Sep. 9, 2015;6:252. doi: 10.3389/fphys.2015. 00252. PMID: 26441672; PMCID: PMC4563167. (Year: 2015).*
Liu M, Zeng X, Ma C, Yi H, Ali Z, Mou X, Li S, Deng Y, He N. Injectable hydrogels for cartilage and bone tissue engineering. Bone Res. May 30, 2017;5:17014. doi: 10.1038/boneres.2017.14. PMID: 28584674; PMCID: PMC5448314. (Year: 2017).*
Afshar Bakooshli M, et al. A 3D culture model of innervated human skeletal muscle enables studies of the adult neuromuscular junction. Elife. May 14, 2019;8:e44530. doi: 10.7554/eLife.44530. PMID: 31084710; PMCID: PMC6516829. (Year: 2019).*
Wiatrak B, Kubis-Kubiak A, Piwowar A, Barg E. PC12 Cell Line: Cell Types, Coating of Culture Vessels, Differentiation and Other Culture Conditions. Cells. Apr. 14, 2020;9(4):958. doi: 10.3390/cells9040958. PMID: 32295099; PMCID: PMC7227003. (Year: 2020).*
B1ONUMB3R5. "Elastic modulus of skeletal muscle." Accessed Jan. 23, 2024. Viewed via Wayback Machine, Internet Archive of Jan. 30, 2020. [https://web.archive.org/web/20200130020945/https://bionumbers.hms.harvard.edu/bionumber.aspx?s=n&v=3&id=106647] (Year: 2020).*
Narayanan, N., Jiang, C., Uzunalli, G et al. Polymeric Electrospinning for Musculoskeletal Regenerative Engineering. Regen. Eng. Transl. Med. 2, 69-84 (2016). https://doi.org/10.1007/s40883-016-0013-8 (Year: 2016).*

(Continued)

*Primary Examiner* — Allison M Fox
*Assistant Examiner* — Alyssa G Weston
(74) *Attorney, Agent, or Firm* — Schwegman Lundberg & Woessner, P.A.

(57) ABSTRACT

A composition for regeneration of skeletal muscle includes a nerve cell secretome or an isolate thereof. An implantable therapeutic material for regeneration of skeletal muscle includes a hydrogel and nerve cells encapsulated within the hydrogel, wherein at least some of the nerve cells are living. A method of regenerating skeletal muscle includes applying the composition or implanting the implantable material adjacent to skeletal muscle myoblasts and/or myogenic cells to regenerate skeletal muscle therefrom.

17 Claims, 26 Drawing Sheets
(7 of 26 Drawing Sheet(s) Filed in Color)
Specification includes a Sequence Listing.

(56) References Cited

OTHER PUBLICATIONS

Li, Jinze, et al., "A high water-content and high elastic dual-responsive polyurethane hydrogel for drug delivery", J. Mater. Chem. B, 2015, 3, 8401, (2015), 8401-8409.

* cited by examiner

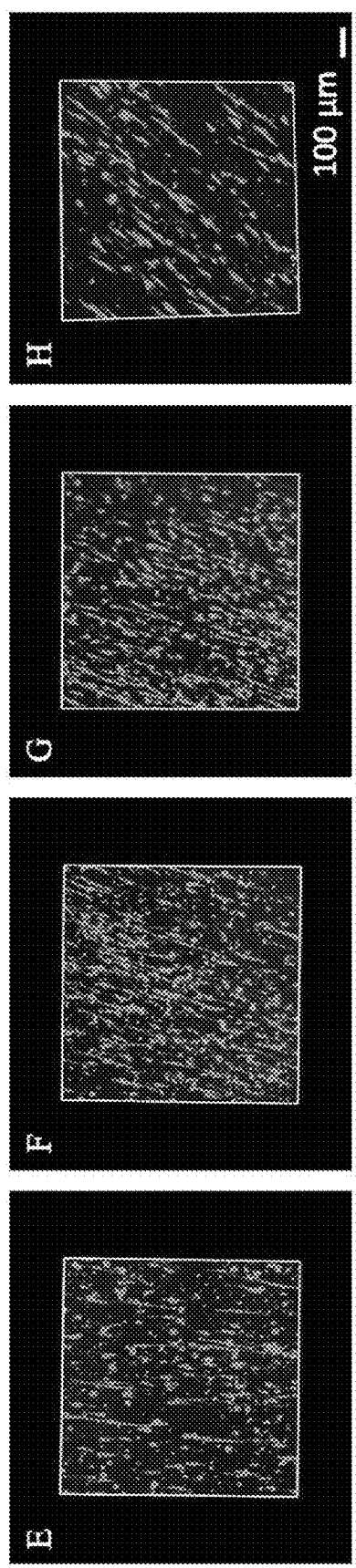

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: A synthetic oligonucleotide sequence

<400> SEQUENCE: 1
agtccctgcc ctttgtacac a                                          21

<210> SEQ ID NO 2
<211> LENGTH: 19
<212> TYPE: DNA
<213> ORGANISM: Artificial Sequence
<220> FEATURE:
<223> OTHER INFORMATION: A synthetic oligonucleotide sequence

<400> SEQUENCE: 2
cgatccgagg gcctcacta                                             19

<210> SEQ ID NO 3
<211> LENGTH: 20
<212> TYPE: DNA
<213> ORGANISM: Artificial Sequence
<220> FEATURE:
<223> OTHER INFORMATION: A synthetic oligonucleotide sequence

<400> SEQUENCE: 3
ggctacgaca ccgcctacta                                            20

<210> SEQ ID NO 4
<211> LENGTH: 20
<212> TYPE: DNA
<213> ORGANISM: Artificial Sequence
<220> FEATURE:
<223> OTHER INFORMATION: A synthetic oligonucleotide sequence

<400> SEQUENCE: 4
cgactctggt ggtgcatctg                                            20
```

```
<210> SEQ ID NO 5
<211> LENGTH: 20
<212> TYPE: DNA
<213> ORGANISM: Artificial Sequence
<220> FEATURE:
<223> OTHER INFORMATION: A synthetic oligonucleotide sequence

<400> SEQUENCE: 5
tgcccagtga atgcaactcc                                              20

<210> SEQ ID NO 6
<211> LENGTH: 20
<212> TYPE: DNA
<213> ORGANISM: Artificial Sequence
<220> FEATURE:
<223> OTHER INFORMATION: A synthetic oligonucleotide sequence

<400> SEQUENCE: 6
ttgggcatgg tttcgtctgg                                              20

<210> SEQ ID NO 7
<211> LENGTH: 21
<212> TYPE: DNA
<213> ORGANISM: Artificial Sequence
<220> FEATURE:
<223> OTHER INFORMATION: A synthetic oligonucleotide sequence

<400> SEQUENCE: 7
ggagaggatt gaggcccaaa a                                            21

<210> SEQ ID NO 8
<211> LENGTH: 21
<212> TYPE: DNA
<213> ORGANISM: Artificial Sequence
<220> FEATURE:
<223> OTHER INFORMATION: A synthetic oligonucleotide sequence

<400> SEQUENCE: 8
cacggtcact ttccctccat c                                            21
```

COMPOSITIONS AND MATERIALS FOR REGENERATION OF SKELETAL MUSCLE

CROSS-REFERENCE TO RELATED APPLICATION

This application claims the benefit of priority to U.S. Provisional Patent Application Ser. No. 63/016,386 filed Apr. 28, 2020, the disclosure of which is incorporated herein in its entirety by reference.

STATEMENT OF GOVERNMENT FUNDING

This invention was made with government support under AR068108 and AR071649 awarded by the National Institutes of Health. The government has certain rights in the invention.

INCORPORATION BY REFERENCE OF SEQUENCE LISTING

A Sequence Listing is provided herewith as a text file. "2116886.txt" created on Feb. 12, 2021 and having a size of 4,096 bytes. The contents of the text file are incorporated by reference herein in their entirety.

BACKGROUND

Regeneration of skeletal muscle injuries resulting from volumetric muscle loss and severe trauma presents a significant clinical challenge. Current cell-based therapies for skeletal muscle regeneration are hindered by low survival and long-term engraftment of the transplanted cells in the injured muscle. Therefore, there is a critical need for developing biomaterial strategies that can provide cellular and structural support in regeneration of new functional skeletal muscles. Reinnervation is a critical component during skeletal muscle regeneration and is a major factor in functional regeneration of skeletal muscle post injury. Nevertheless, severe muscle injuries lack reinnervation, which leads to impaired functioning of regenerated muscle tissue.

There is a growing interest to harness cell-secreted signaling factors for regenerative engineering applications. For example, cell-secreted signaling factors from adipose-derived stem cells, endothelial progenitor cells, and embryonic stem cells have been previously reported for preclinical trials to treat cardiovascular diseases and injuries. Although nerve cell secretome has been previously used to modulate differentiation of mesenchymal stem cells (MSCs), little is known on how nerve cell secretome affects myoblasts and skeletal muscle regeneration.

SUMMARY OF THE INVENTION

A composition for regeneration of skeletal muscle includes a nerve cell secretome or an isolate thereof.

A medical implant includes a composition for regeneration of skeletal muscle that includes a nerve cell secretome or an isolate thereof.

An implantable therapeutic material for regeneration of skeletal muscle includes a hydrogel and nerve cells encapsulated within the hydrogel, wherein at least some of the nerve cells are living.

A medical implant includes an implantable therapeutic material for regeneration of skeletal muscle that includes a hydrogel and nerve cells encapsulated within the hydrogel, wherein at least some of the nerve cells are living.

A method of forming an implantable therapeutic material includes adding nerve cells to a hydrogel precursor composition. The method includes forming the hydrogel from the hydrogel precursor composition to form the implantable therapeutic material. The implantable therapeutic material includes a hydrogel and nerve cells encapsulated within the hydrogel, wherein at least some of the nerve cells are living.

A method of regenerating skeletal muscle includes applying a composition for regeneration of skeletal muscle adjacent to skeletal muscle myoblasts and/or myogenic cells to regenerate skeletal muscle therefrom. The composition includes a nerve cell secretome or an isolate thereof.

A method of regenerating skeletal muscle includes implanting a medical implant adjacent to skeletal muscle myoblasts and/or myogenic cells to regenerate skeletal muscle therefrom. The medical implant includes a composition for regeneration of skeletal muscle that includes a nerve cell secretome or an isolate thereof.

A method of regenerating skeletal muscle includes implanting an implantable material adjacent to skeletal muscle myoblasts and/or myogenic cells to regenerate skeletal muscle therefrom. The implantable material includes hydrogel and nerve cells encapsulated within the hydrogel, wherein at least some of the nerve cells are living.

A method of regenerating skeletal muscle includes implanting a medical implant adjacent to skeletal muscle myoblasts and/or myogenic cells to regenerate skeletal muscle therefrom. The medical implant includes an implantable therapeutic material for regeneration of skeletal muscle that includes a hydrogel and nerve cells encapsulated within the hydrogel, wherein at least some of the nerve cells are living.

BRIEF DESCRIPTION OF THE FIGURES

The patent or application file contains at least one drawing executed in color. Copies of this patent or patent application publication with color drawing(s) will be provided by the Office upon request and payment of the necessary fee.

The drawings illustrate generally, by way of example, but not by way of limitation, various embodiments of the present invention.

FIG. 3D top row illustrates live/dead assay illustrating the viability of myoblasts when cultured in SF, 300 k, 1M and 5M at day 3, in accordance with various embodiments. FIG. 3D bottom row illustrates confocal micrographs by MHC staining illustrating the myotube formation after 4 days of differentiation in SF, 300 k, 1M and 5M, in accordance with various embodiments.

FIG. 5E-H illustrate representative confocal micrographs of live/dead assay at day 5 for myoblasts treated with (5E) SF. (5F) secretome obtained from the 300 k group. (5G) secretome obtained from the 1M group, and (5H) secretome obtained from the 5M group, in accordance with various embodiments.

DETAILED DESCRIPTION OF THE INVENTION

Figure 1A:
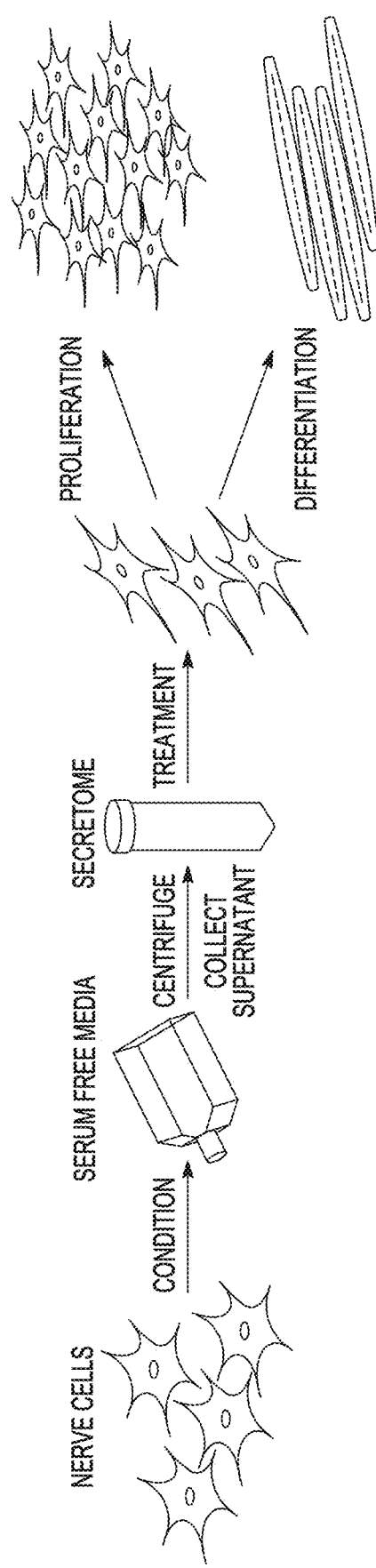
FIG. 1A shows schematics illustrating treatment of myoblasts on 2D TCPS with the PC12-derived secretome, in accordance with various embodiments.

Reference will now be made in detail to certain embodiments of the disclosed subject matter. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X. Y, or about Z" has the same meaning as "about X, about Y, or about Z." unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A. B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

In the methods described herein, the acts can be carried out in any order without departing from the principles of the invention, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range, and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%. The term "substantially free of" as used herein can mean having none or having a trivial amount of, such that the amount of material present does not affect the material properties of the composition including the material, such that about 0 wt % to about 5 wt % of the composition is the material, or about 0 wt % to about 1 wt %, or about 5 wt % or less, or less than, equal to, or greater than about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less, or about 0 wt %.

As used herein, the term "polymer" refers to a molecule having at least one repeating unit and can include copolymers.

Composition for Regeneration of Skeletal Muscle.

A composition for regeneration of skeletal muscle can include a nerve cell secretome or an isolate thereof. The nerve cell secretome is the set of proteins expressed by a nerve cell and secreted into the extracellular space of the nerve cell. The isolate thereof can include any suitable one or more proteins from the nerve cell secretome such that the isolate provides regeneration of skeletal muscle. The isolate can be isolated from the nerve cell secretome in any suitable way.

The nerve cell secretome or isolate thereof can be any suitable proportion of the composition, such as 0.001 wt % to 100 wt %, or 0.001 wt % to 50 wt %, or 50 wt % to 100 wt %, or less than, equal to, or greater than 0.001 wt %, 0.005, 0.01, 0.05, 0.1, 0.5, 1, 2, 4, 6, 8, 10, 20, 30, 40, 50, 60, 70, 80, 90, 92, 94, 96, 98, or 99 wt % or more. The composition can be an aqueous composition. The composition can be an injectable composition.

The nerve cell secretome or the isolate thereof can include one or more signaling factors that are effective to modulate skeletal muscle cell behavior. When contacted with myoblasts and/or myogenic cells, the nerve cell secretome or the isolate thereof is effective to regenerate skeletal muscle. The nerve cell secretome or the isolate thereof can be effective to promote regeneration of skeletal muscle, promote innervation of skeletal muscle, or a combination thereof. The nerve cell secretome or the isolate thereof can be effective to promote survival and proliferation of myoblasts and/or myogenic cells, promote myofiber formation, promote muscle innervation, promote angiogenesis, or a combination thereof.

The nerve cell secretome can include Galectin-1, Progranulin, CathepsinB, Glypican-1, Prosaposin, or a combination thereof. The nerve cell secretome isolate can include Galectin-1, Progranulin, CathepsinB, Glypican-1, Prosaposin, or a combination thereof.

The nerve cells from which the secretome is produced can be any suitable one or more nerve cells, such as a unipolar nerve cell, a biopolar nerve cell, a multipolar nerve cell, an anaxonic nerve cell, a psudounipolar nerve cell, a basket nerve cell, a Betz nerve cell, a Lugaro nerve cell, a medium spiny nerve cell, a Purkinje nerve cell, a Renshaw nerve cell, a unipolar brush nerve cell, a granule nerve cell, an anterior horn nerve cell, a spindle nerve cell, an afferent nerve cell, an efferent nerve cell, an interneuron nerve cell, a cholinergic nerve cell, an adrenergic nerve cell, a GABAergic nerve cell, a glutamatergic nerve cell, a dopaminergic nerve cell, a serotonergic nerve cell, a purinergic nerve cell, a histaminergic nerve cell, a catecholamine nerve cell, or a combination thereof. The nerve cells can include a catecholamine nerve cell (i.e., secretes catecholamine). The nerve cells can include an adrenal pheochromocytoma (PC12) cell line (i.e., a cell line derived from a pheochromocytoma of the rat adrenal medulla, that have an embryonic origin from the neural crest that has a mixture of neuroblastic cells and eosinophilic cells1).

The nerve cell secretome can be produced from a culture of the nerve cells having any suitable concentration in the culture media thereof. For example, the nerve cell secretome can be a secretome from a culture of the nerve cells having a concentration of the nerve cells in culture media of $1 \times 10^3$ to $1 \times 10^{10}$ nerve cells per 10 mL of the culture media, $1 \times 10^4$ to $1\times10^7$ of the nerve cells per 10 mL, $3\times10^5$ to $5\times10^6$ of the nerve cells per 10 mL, $1\times10^3$ to $9\times10^6$ of the nerve cells per 10 mL, $5\times10^5$ to $4\times10^6$ of the nerve cells per 10 mL, $2\times10^6$ to $1\times10^7$ of the nerve cells per 10 mL, or greater than, equal to, or less than $1\times10^3$ of the nerve cells per 10 mL, $1\times10^4$, $1\times10^5$, $1\times10^6$, $1\times10^7$, $1\times10^8$, $1\times10^9$, or $1\times10^{10}$ of the nerve cells per 10 mL of the culture media.

Medical Implant Including Composition.

A medical implant can include the composition for regeneration of skeletal muscle that includes a nerve cell secretome or an isolate thereof. The implant can be any suitable implant for implantation adjacent to a site of desired muscle regeneration.

The medical implant can further include a fiber scaffold, such as a synthetic fiber scaffold. The fiber scaffold can mimic the native microenvironment of skeletal muscle. The fiber scaffold can be a polymeric fiber scaffold. For example, the fiber scaffold can include a polyester, tissue culture polystyrene (TCPS), poly(lactide-co-glycolide), or a combination thereof. The fiber scaffold can be an electrospun fiber scaffold.

The fiber scaffold can include skeletal muscle myoblasts and/or myogenic cells. At least some of the skeletal muscle myoblasts and/or myogenic cells can be added to and/or cultured on the fiber scaffold prior to implantation of the medical implant.

Implantable Therapeutic Material.

An implantable therapeutic material for regeneration of skeletal muscle can include a hydrogel and nerve cells encapsulated within the hydrogel, wherein at least some of the nerve cells are living. The implantable therapeutic material can be the hydrogel with nerve cells therein, or the implantable therapeutic material can include one or more other optional components.

The hydrogel can be a three dimensional matrix that encapsulates the nerve cells, allowing them to live and produce nerve cell secretome after implantation such that the hydrogel encapsulating the nerve cells produces the nerve cell secretome, thereby providing therapeutic regeneration of muscle at the site of implantation. The nerve cells can be any suitable one or more nerve cells, such as a unipolar nerve cell, a biopolar nerve cell, a multipolar nerve cell, an anaxonic nerve cell, a psudounipolar nerve cell, a basket nerve cell, a Betz nerve cell, a Lugaro nerve cell, a medium spiny nerve cell, a Purkinje nerve cell, a Renshaw nerve cell, a unipolar brush nerve cell, a granule nerve cell, an anterior horn nerve cell, a spindle nerve cell, an afferent nerve cell, an efferent nerve cell, an interneuron nerve cell, a cholinergic nerve cell, an adrenergic nerve cell, a GABAergic nerve cell, a glutamatergic nerve cell, a dopaminergic nerve cell, a serotonergic nerve cell, a purinergic nerve cell, a histaminergic nerve cell, a catecholamine nerve cell, or a combination thereof. The nerve cells can include a catecholamine nerve cell. The nerve cells can include an adrenal pheochromocytoma (PC12) cell line. The nerve cell secretome can include Galectin-1, Progranulin, CathepsinB, Glypican-1, Prosaposin, or a combination thereof.

The hydrogel can be any suitable hydrogel. The hydrogel can be a reaction product of polyvinyl alcohol, polyethylene glycol, sodium polyacrylate, an acrylate polymer, an acrylate copolymer, polylactic acid, a polylactic acid copolymer, polyglycolic acid, a polyglycolic acid copolymer, poly(lactic-co-glycolic acid), poly(amino acids), polyphosphazenes, poly(phosphoesters), collagen, gelatin, fibrin, agarose, chitosan, cellulose, a cellulose derivative, methylcellulose, hyaluronan (i.e., hyaluronic acid), elastin, dextran, chondroitin sulfate, agarose, alginate, heparin, an elastin-like-polypeptide (ELP), or a combination thereof. The hydrogel can be a reaction product of hyaluronic acid, chondroitin sulfate, polyethylene glycol or a copolymer thereof, or a combination thereof. The hydrogel can be a reaction product of starting materials including hyaluronic acid, chondroitin sulfate, and polyethylene glycol. The hydrogel can be a reaction product of thiolated hyaluronic acid and chondroitin sulfate that is cross-linked with polyethylene glycol via thiol-ene click chemistry. The composition that is reacted to form the hydrogel can be referred to as a hydrogel precursor composition.

The hydrogel can have any suitable concentration of the nerve cells therein. For example, the hydrogel can have a concentration of the nerve cells of 10,000 cells per 20 microliters of the hydrogel to 10,000,000 cells per 20 microliters of the hydrogel, 100,000 cells per 20 microliters of the hydrogel to 2,000,000 cells per 20 microliters of the hydrogel, 200,000 cells per 20 microliters of the hydrogel to 1,000,000 cells per 20 microliters of the hydrogel, or less than, equal to, or greater than 10,000, 50,000, 100,000, 200,000, 300,000, 400,000, 500,000, 600,000, 750,000, 1,000,000, 1,500,000, 2,000,000, 5,000,000, or 10,000,000 cells per 20 microliters of the hydrogel.

The hydrogel can have any suitable storage modulus. The hydrogel can have a storage modulus that is approximately the same as soft tissue, such as soft tissue at or near the site of implantation (e.g., the hydrogel can mimic the storage modulus of soft tissue). The hydrogel can have a storage modulus of 20 kPa or less, or 16 kPa or less, or 10 kPa to 16 kPa, 12 kPa to 14 kPa, 12.5 kPa to 13.5 kPa, or less than, equal to, or greater than 10 kPa, 10.5, 11, 11.5. 12, 12.5, 13, 13.5, 14, 14.5, 15, 15.5, or 16 kPa. In some embodiments, the hydrogel can be injectable.

Medical Implant Including Implantable Therapeutic Material.

A medical implant can include the implantable therapeutic material for regeneration of skeletal muscle that includes a hydrogel and nerve cells encapsulated within the hydrogel, wherein at least some of the nerve cells are living. The medical implant can be any suitable medical implant. The medical implant can be suitable for implantation at or near a site of desired muscle regeneration.

The medical implant can further include a fiber scaffold, such as a synthetic fiber scaffold. The fiber scaffold can be in contact with the implantable therapeutic material. The fiber scaffold can mimic the native microenvironment of skeletal muscle. The fiber scaffold can be a polymeric fiber scaffold. For example, the fiber scaffold can include a polyester, tissue culture polystyrene (TCPS), poly(lactide-co-glycolide), or a combination thereof. The fiber scaffold can be an electrospun fiber scaffold.

The fiber scaffold can include skeletal muscle myoblasts and/or myogenic cells. At least some of the skeletal muscle myoblasts and/or myogenic cells can be added to and/or cultured on the fiber scaffold prior to implantation of the medical implant.

Figure 13:
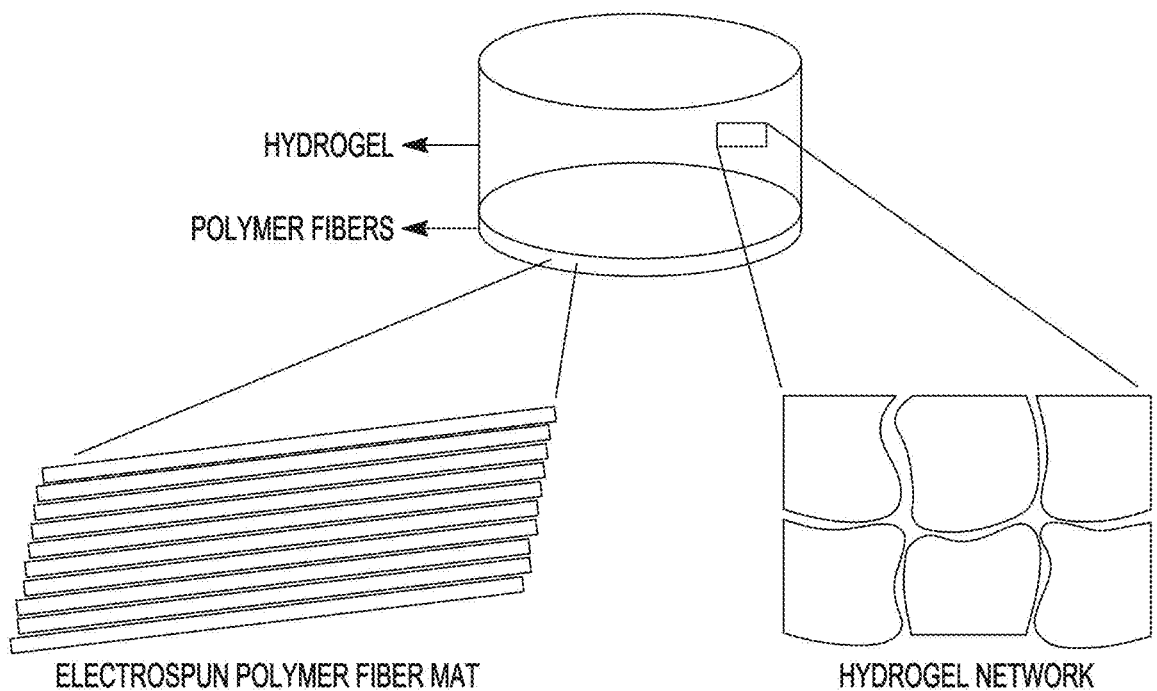
FIG. 13 is an illustration of a hydrogel having living nerve cells incorporated therein on top of an electrospun polymer fiber mat, in accordance with various embodiments.

FIG. 13 is an illustration of a hydrogel having living nerve cells incorporated therein on top of an in contact with an electrospun polymer fiber mat, in accordance with various embodiments.

Method of Forming Implantable Therapeutic Material.

A method of forming an implantable therapeutic material can include adding nerve cells to a hydrogel precursor composition. The method can include forming the hydrogel from the hydrogel precursor composition to form the implantable therapeutic material. The implantable therapeutic material can include a hydrogel and nerve cells encapsulated within the hydrogel, wherein at least some of the nerve cells are living. The method can include allowing the nerve cells to multiply (e.g., culturing the cells) within the hydrogel (e.g., within the implantable therapeutic material).

Method of Regenerating Skeletal Muscle.

A method of regenerating skeletal muscle can include applying the composition for regeneration of skeletal muscle adjacent to skeletal muscle myoblasts and/or myogenic cells to regenerate skeletal muscle therefrom. The composition includes a nerve cell secretome or an isolate thereof.

The applying can be any suitable applying. The applying can include injecting the composition into skeletal muscle or adjacent thereto, implanting an implant that releases the composition to the skeletal muscle myoblasts and/or myogenic cells, or a combination thereof. The applying can include applying the composition adjacent to an implanted fiber scaffold.

The method can further include implanting the fiber scaffold. The fiber scaffold can be a synthetic fiber scaffold. The fiber scaffold can be in contact with the implantable therapeutic material after injection thereof. The fiber scaffold can mimic the native microenvironment of skeletal muscle. The fiber scaffold can be a polymeric fiber scaffold. For example, the fiber scaffold can include a polyester, tissue culture polystyrene (TCPS), poly(lactide-co-glycolide), or a combination thereof. The fiber scaffold can be an electrospun fiber scaffold.

The fiber scaffold can include skeletal muscle myoblasts and/or myogenic cells. At least some of the skeletal muscle myoblasts and/or myogenic cells can be added to and/or cultured on the fiber scaffold prior to implantation of the fiber scaffold, prior to applying the composition for regeneration of skeletal muscle adjacent to the myoblasts and/or myogenic cells, or a combination thereof.

A method of regenerating skeletal muscle can include implanting a medical implant adjacent to skeletal muscle myoblasts and/or myogenic cells to regenerate skeletal muscle therefrom, wherein the medical implant includes the composition for regeneration of skeletal muscle that includes a nerve cell secretome or an isolate thereof.

A method of regenerating skeletal muscle can include implanting an implantable therapeutic material adjacent to skeletal muscle myoblasts and/or myogenic cells to regenerate skeletal muscle therefrom, wherein the implantable material includes hydrogel and nerve cells encapsulated within the hydrogel, wherein at least some of the nerve cells are living.

A method of regenerating skeletal muscle can include implanting a medical implant adjacent to skeletal muscle myoblasts and/or myogenic cells to regenerate skeletal muscle therefrom, wherein the medical implant includes the implantable therapeutic material for regeneration of skeletal muscle that includes a hydrogel and nerve cells encapsulated within the hydrogel, wherein at least some of the nerve cells are living.

The method of regenerating skeletal muscle can include implanting the medical implant or implantable therapeutic material adjacent to skeletal muscle myoblasts and/or myogenic cells to regenerate skeletal muscle therefrom. After the implanting, the implantable material or medical implant including the implantable material can release secretome from the nerve cells in the hydrogel which regenerate skeletal muscle from the myoblasts and/or myogenic cells. After the implanting, the nerve cells can grow and propagate in the hydrogel. The implanting can be effective to promote regeneration of skeletal muscle, promote innervation of skeletal muscle, or a combination thereof. The implanting of the medical implant or implantable therapeutic material can be effective to promote survival and proliferation of myoblasts and/or myogenic cells, promote myofiber formation, promote muscle innervation, promote angiogenesis, or a combination thereof.

EXAMPLES

Various embodiments of the present invention can be better understood by reference to the following Examples which are offered by way of illustration. The present invention is not limited to the Examples given herein.

Part 1. Harnessing Nerve-Muscle Cell Interactions for Biomaterials-Based Skeletal Muscle Regeneration.

Materials and Methods.

Materials: All chemicals and cell culture reagents were purchased from Sigma-Aldrich and Thermo Fisher Scientific, respectively, unless otherwise stated.

Cell culture and maintenance: PC12 cells (neuronal model cell) were cultured and maintained in growth media consisting of High glucose DMEM supplemented with 10% horse serum, 5% fetal bovine serum (FBS) and 1% penicillin/streptomycin. Similarly. C2C12 myoblast cells were cultured and maintained in growth media consisting of high glucose DMEM supplemented with 10% FBS and 1% penicillin/streptomycin. The cells were cultured at 37° C. in 95% humidified air and 5% $CO_2$ for various periods of time. The media was changed every other day.

PC12 secretome preparation: To obtain conditioned media. PC12 cells were cultured in 75 $cm^2$ flask until they reached the required confluency. FIG. 1A shows schematics illustrating treatment of myoblasts on 2D TCPS with the PC12-derived secretome. The cells were detached from the surface using a cell scraper, pelleted, and subsequently washed in calcium free phosphate buffer saline (PBS) to remove growth media. Next, PC12 were counted and reseeded with three cell densities ($3\times10^5$, $1\times10^6$, and $5\times10^6$ cells per 10 mL denoted by 300 k, 1M. and 5M, respectively) in serum-free (SF) DMEM. After 24 h of incubation, the secretome was collected by centrifugation to remove cell debris. The secretome was passed through a sterile 0.22 μm filter and used for cell studies.

C2C12 proliferation and differentiation: Myoblast responses on both 2D TCPS and 3D aligned electrospun fiber scaffolds were characterized using cell culture media supplemented with secretome collected from PC12 cells with varying cell densities of 300 k, 1M, and 5M (FIG. 1A). In brief, C2C12 myoblasts were seeded at a density of $1\times10^4$ cells per well in a 24-well plate or $2\times10^4$ per fiber scaffold and allowed to attach overnight. After overnight attachment, the media was removed, and the cells were washed with calcium free PBS twice to remove remaining media. Then the cells were treated with either SF media or SF media supplemented with PC12 secretome. The metabolic activity of cells was measured at days 1, 3, and 5 using MTS assay (Promega). For the differentiation studies, C2C12 myoblasts were seeded at a density of $1\times10^5$ cells per well in a 24-well plate or $2\times10^5$ per fiber scaffold and allowed to attach overnight forming confluent monolayer of myoblasts. Then, the cells were treated with either SF or PC12 secretome. Cells were supplemented with fresh media every other day. The cells were allowed to differentiate for four days before collecting the samples for immunofluorescent staining and quantitative PCR (qPCR) for myogenic differentiation markers including MyoD, MyoG, and MYH8.

PC12 cell encapsulation and characterization in hydrogel: HCP hydrogels were synthesized via thiol-ene click chemistry using a previously reported method. Briefly, thiol-modified HA and CS were separately dissolved in degassed, sterile PBS. The polymers were then cross-linked with PEGDA (Alfa Aesar, molecular weight—3400) by the -ene functional group at the terminal ends under a temperature of 37° C., thus resulting in the formation of the HCP hydrogel. Polymer molecular structure was confirmed by nuclear magnetic resonance (NMR) spectroscopy. Rheological experiments were carried out with a TA Discovery Series Hybrid Rheometer (DHR)-3. Morphology and structure of HA-CS hydrogel were examined using a cryo-SEM (FEI Nano Nova SEM). Hydrogel cell density was controlled by the cells present in the cell pellet; cell densities of $2 \times 10^5$ (200 k group), $5 \times 10^5$ (500 k group), and $1 \times 10^6$ (1M group) seeded in 20 µL hydrogel were used in the study. These three cell densities were used to retain cell number to culture media volume ratios ($1.33 \times 10^5$ cells per mL, $3.33 \times 10^5$ cells per mL, $6.66 \times 10^5$ cells per mL of culture media for 200 k, 500 k and 1M groups, respectively) comparable to that of secretome obtained from 5M cells ($5 \times 10^5$ cells per mL of media). Cell-encapsulated hydrogels were placed in 24-well plates and supplemented with culture media to facilitate cell growth. Cell growth of the encapsulated cells was evaluated using MTS assay at predetermined time points of 1, 3 and 7 days. Viability of the cells was characterized using a live/dead assay. Morphology of the encapsulated cells was characterized at predetermined time points of day 1, 3 and 7 using CytoPainter phalloidin iFluor 555 (Abcam) as per manufacturer's instruction.

Co-culture transwell studies: For the co-culture studies, myoblasts were seeded in a 24-well plate and allowed to attach overnight. Simultaneously, hydrogels encapsulating PC12 cells were formulated and incubated overnight in a separate 24-well plate. Cell culture inserts were attached on the myoblast-seeded plates and the hydrogel was placed on the insert. Then, 1.5 mL SF media was supplemented to the co-culture and the cells were allowed to proliferate for 5 days and differentiate for 4 days. Cell growth was monitored using MTS assay and differentiation was characterized using immunofluorescence staining and qPCR. The viability of the PC12 cells was evaluated using Live/Dead assay.

Proteomics analysis of the secretome: Samples for proteomics analysis were prepared as mentioned in the supplementary information. Peptide samples were analyzed using a Dionex UltiMate 3000 RSLC nano System (Thermo Fisher Scientific, Odense, Denmark) coupled on-line to Q_Exactive High Field Quadrupole Hybrid Orbitrap Mass Spectrometer (Thermo Fisher Scientific, Waltham, MA, USA). Parameters for the LC/MS/MS run were set as previously reported. The full scan MS spectra were collected in the range of 400-1600 m/z at a resolution of 120,000 at 200 m/z. MS/MS data were collected at 15,000 resolutions using an HCD fragmentation. The LC-MS/MS data analysis was performed using MaxQuant software and the andromeda search engine. The spectra were searched against UniProtKB *Rattus rattus* protein database for protein identification and label-free relative quantitation. Default MaxQuant settings were used except the following parameters: 10 ppm precursor mass (MS) tolerance, 20 ppm fragment mass (MS/MS) tolerance, enzyme specificity for trypsin/Lys-C, allowing up to two missed cleavages. Oxidation of methionine (M) was defined as a variable modification, and iodoethanol of cysteine (C) was defined as a fixed modification for database searches. The 'unique plus razor peptides' were used for peptide quantitation and the false discovery rate (FDR) of both peptides spectral match (PSM) and proteins identification was set at 0.01. Proteins labeled either as contaminants or reverse hits were removed from the analysis. Similarly, proteins identified without any quantifiable peak (0 intensity) and those identified by a single MS/MS count were also removed from downstream analyses.

Statistical analysis: All the experiments were run in triplicate per sample. Quantitative data presented in the study were reported as mean±standard deviation (SD). Statistical analysis was performed using one-way analysis of variance (one-way ANOVA). Comparison between the two means was determined using the Tukey test with a minimum confidence level of $p<0.05$ for statistical significance.

Results.

Figure 1B:
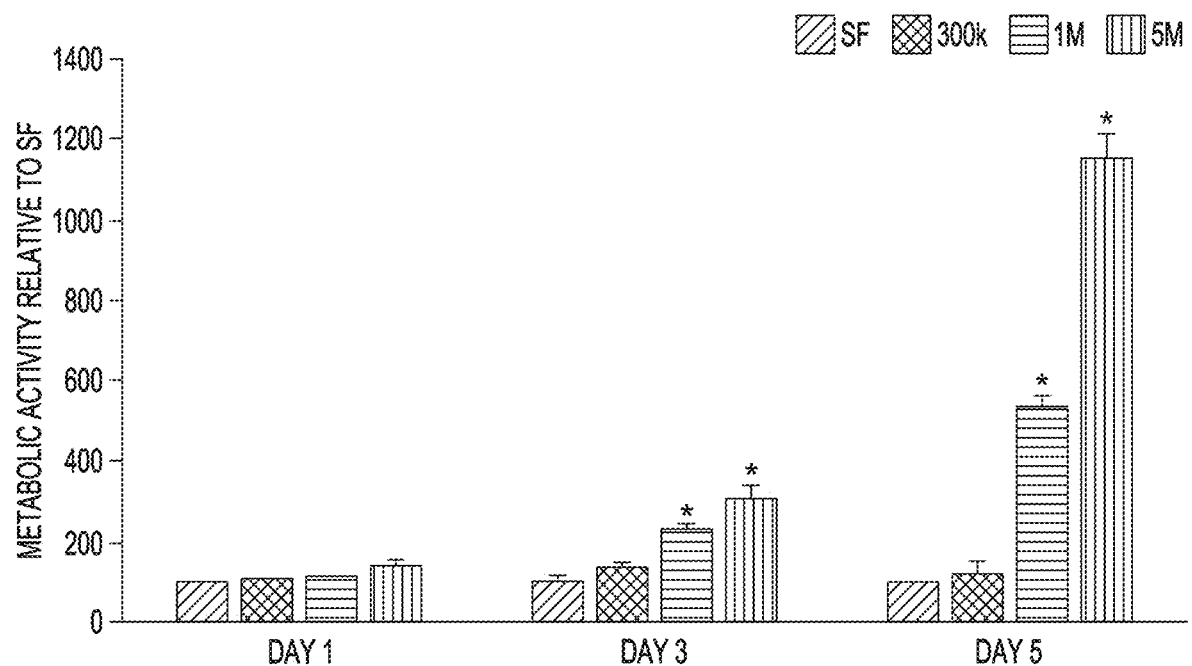
FIG. 1B illustrates an MTS assay showing a significant increase in metabolic activity of myoblasts on TCPS when treated with 1M and 5M cell secretome as compared to SF at day 3 and day 5 ($*p<0.05$), in accordance with various embodiments.
Figure 1C:
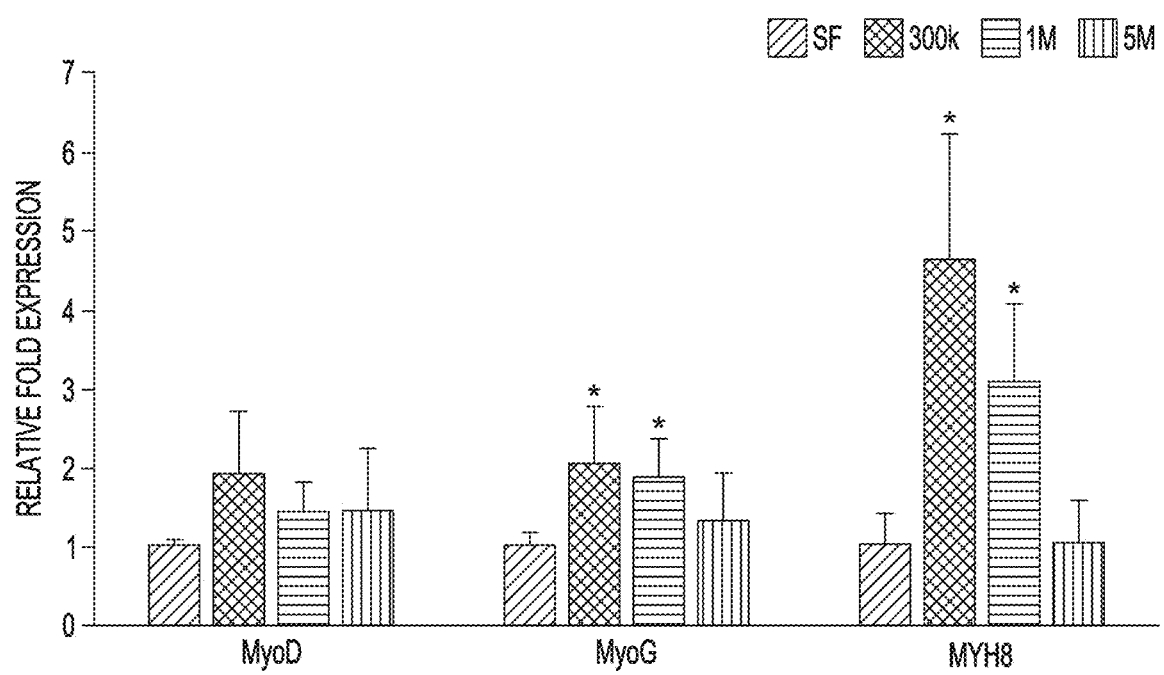
FIG. 1C illustrates gene expression analysis by qPCR demonstrating a significant increase in expression of MyoG and MYH8 after treating with 300 k and 1M cell secretome as compared to SF ($*p<0.05$), in accordance with various embodiments.
Figure 2A:
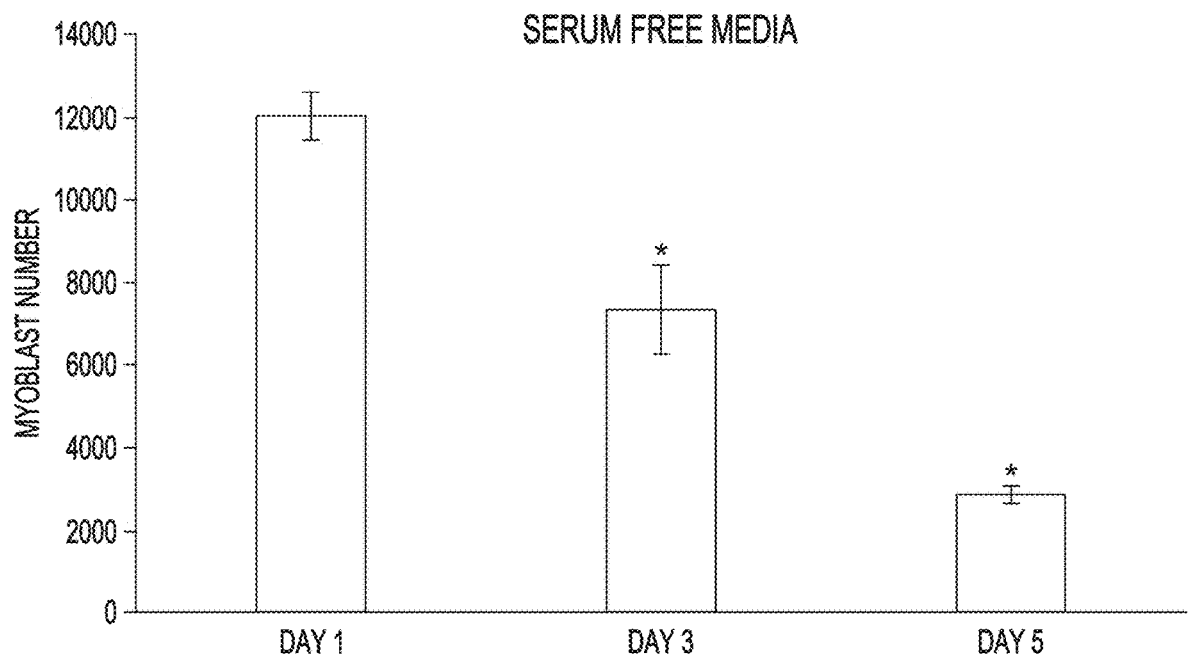
FIG. 2A illustrates an MTS assay showing changes of myoblast cell numbers on 2D TCPS during culture with SF media, in accordance with various embodiments.
Figure 2B:
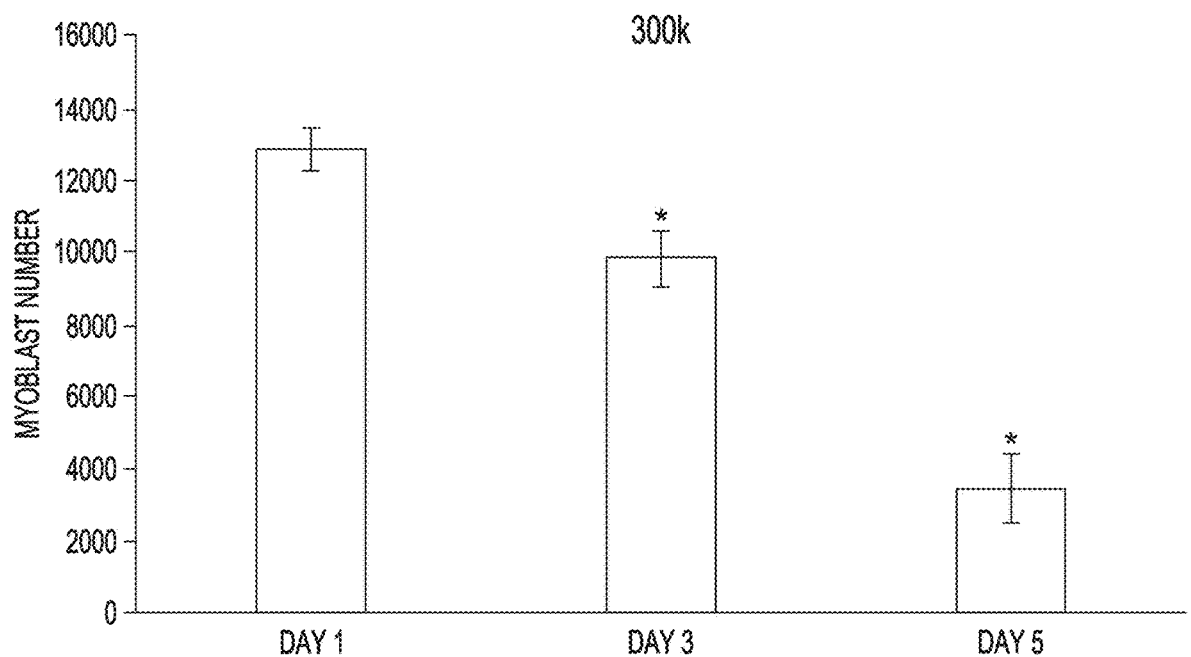
FIG. 2B illustrates an MTS assay showing changes of myoblast cell numbers on 2D TCPS during culture with secretome obtained from the 300 k group, in accordance with various embodiments.
Figure 2C:
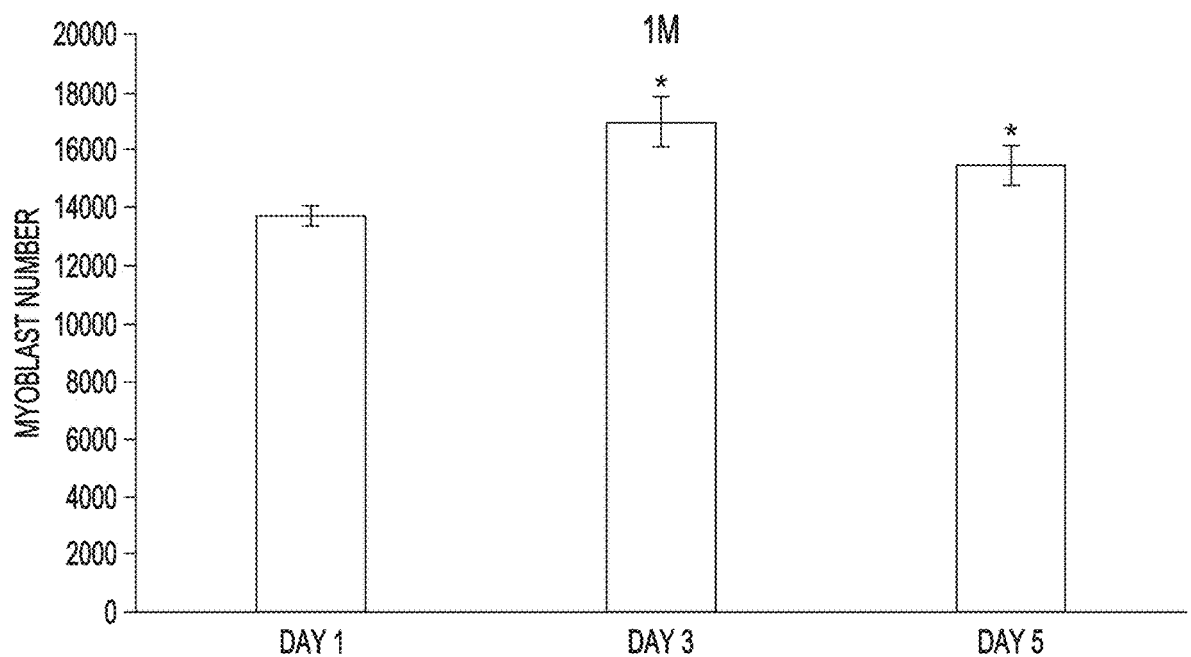
FIG. 2C illustrates an MTS assay showing changes of myoblast cell numbers on 2D TCPS during culture with secretome obtained from the 1M group, in accordance with various embodiments.
Figure 2D:
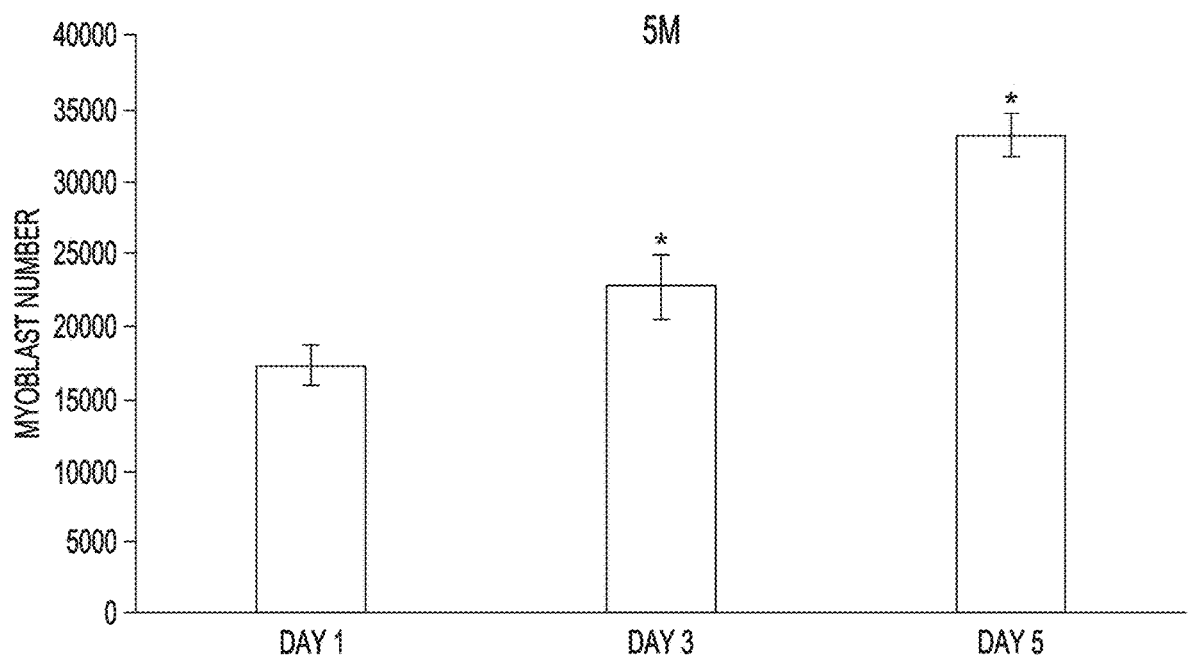
FIG. 2D illustrates an MTS assay showing changes of myoblast cell numbers on 2D TCPS during culture with secretome obtained from the 5M group, in accordance with various embodiments.
Figure 2H:
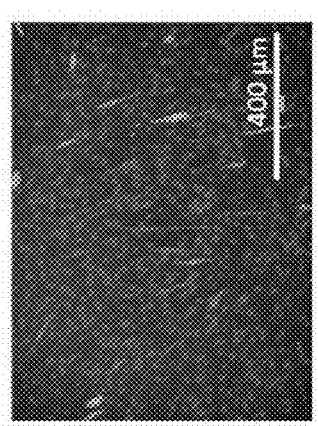
FIG. 2E-H illustrate representative fluorescent micrographs showing myotube formation in (E) SF, (F) Secretome obtained from the 300 k group, (G) Secretome obtained from the 1M group, and (H) Secretome obtained from the 5M group, with green=MHC and blue=nuclei, in accordance with various embodiments.
Figure 2G:
Figure 2F:
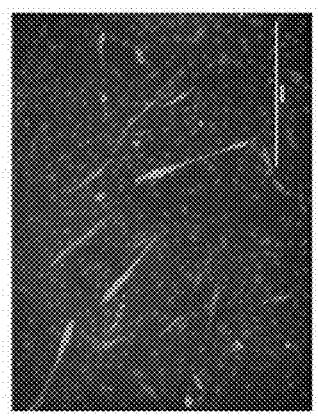
Figure 2E:
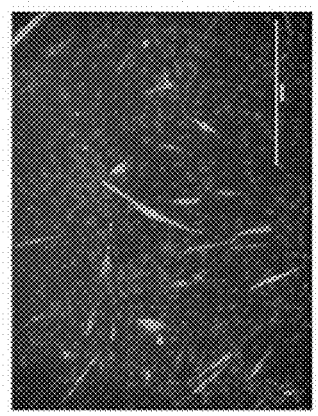

PC12 secretome treatment on myoblasts with 2D culture: MTS results revealed a significant increase in metabolic activity of cells on TCPS treated with secretome obtained from 1M and 5M compared to SF and 300 k at day 3 and day 5, as shown in FIG. 1B. Furthermore, serum starvation resulted in a significant decrease in cell numbers during culture. FIG. 2A illustrates an MTS assay showing changes of myoblast cell numbers on 2D TCPS during culture with SF media. FIG. 2B illustrates an MTS assay showing changes of myoblast cell numbers on 2D TCPS during culture with secretome obtained from the 300 k group. FIG. 2C illustrates an MTS assay showing changes of myoblast cell numbers on 2D TCPS during culture with secretome obtained from the 1M group. FIG. 2D illustrates an MTS assay showing changes of myoblast cell numbers on 2D TCPS during culture with secretome obtained from the 5M group. FIG. 2E-H illustrate representative fluorescent micrographs showing myotube formation in (E) SF, (F) secretome obtained from the 300 k group, (G) secretome obtained from the 1M group, and (H) secretome obtained from the 5M group, with green=MHC and blue=nuclei. Interestingly, a significant increase in cell number was found for myoblasts treated with secretome obtained with 5M indicating progressive cell growth during culture, which suggested beneficial effects of secretome on myoblast proliferation under serum starvation. After 4 days of differentiation, qPCR analysis showed that treatment with secretome obtained from 300 k and 1M resulted in a significant increase in MyoG and MYH8 expression of myoblasts as compared to SF, as shown in FIG. 1C. In contrast, no significant changes in gene expression of MyoG and MYH8 were observed for myoblasts treated with secretome obtained from 5M as compared to those treated with SF. Immunofluorescent staining for MHC confirmed a similar finding with enhanced differentiation of myoblasts treated with secretome from 300 k and 1M (FIGS. 2A-H). Thus, secretome obtained from 5M promoted proliferation of myoblasts while secretome derived from 300 k and 1M enhanced differentiation of myoblasts.

Figure 3A:
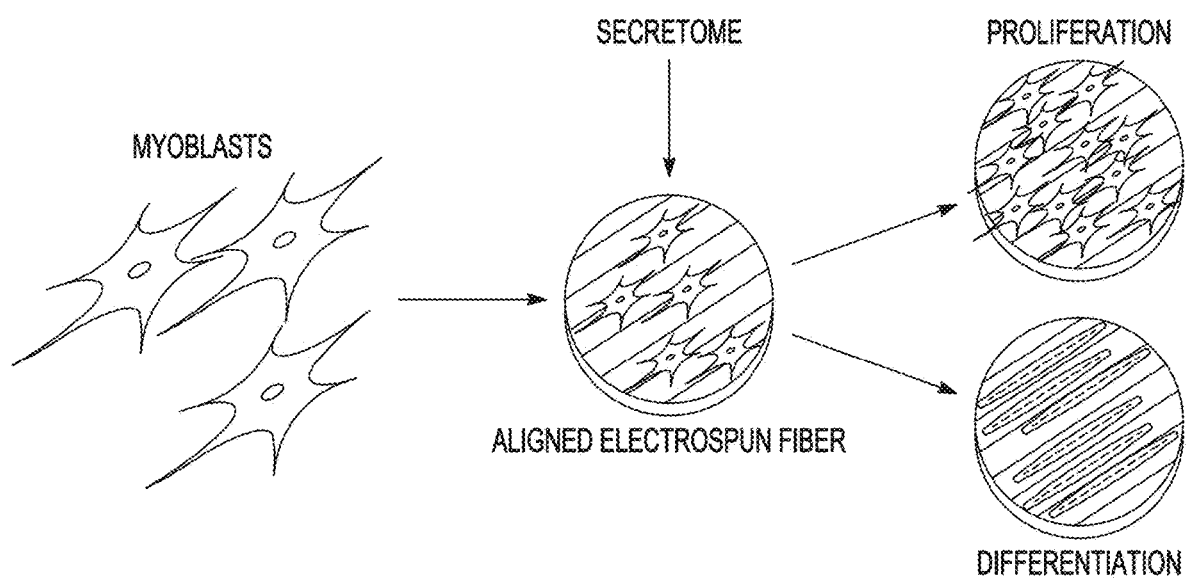
FIG. 3A shows schematics illustrating the treatment of myoblasts on 3D aligned electrospun fiber scaffold with the PC12-derived secretome, in accordance with various embodiments.
Figure 3B:
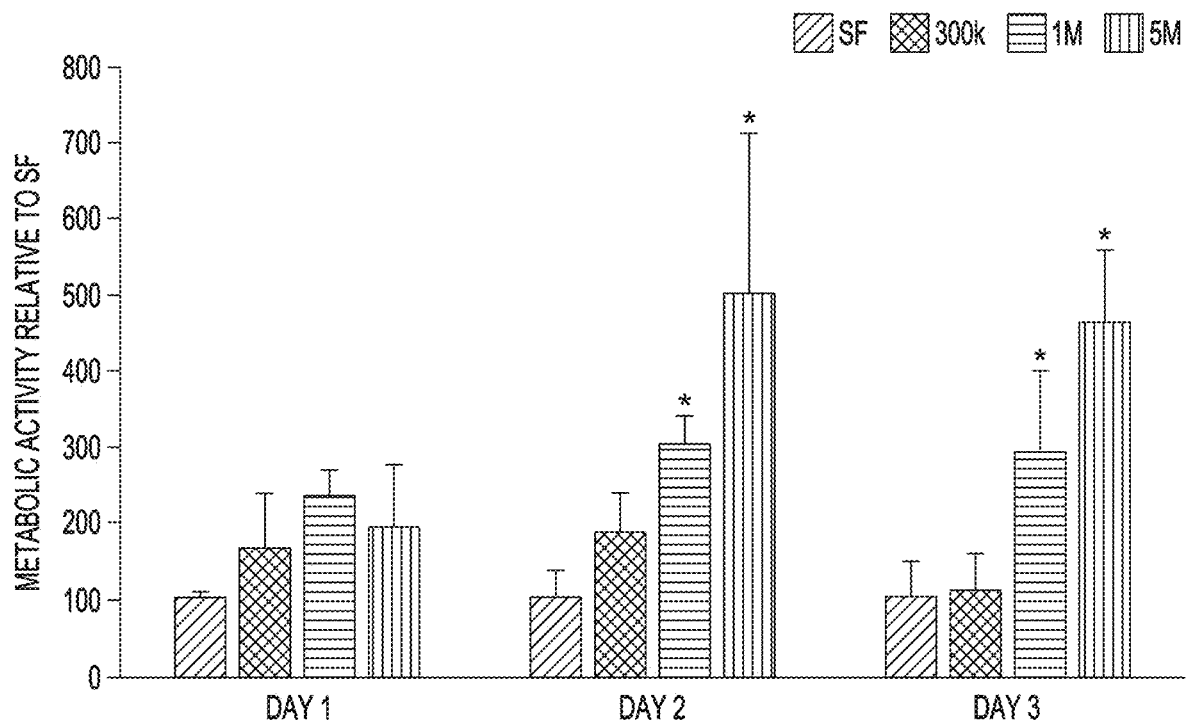
FIG. 3B illustrates an MTS assay showing a significant increase in metabolic activity of myoblasts cultured on aligned fibers when treated with 1M and 5M cell secretome compared to SF at day 3 and day 5 ($*p<0.05$), in accordance with various embodiments.
Figure 3C:
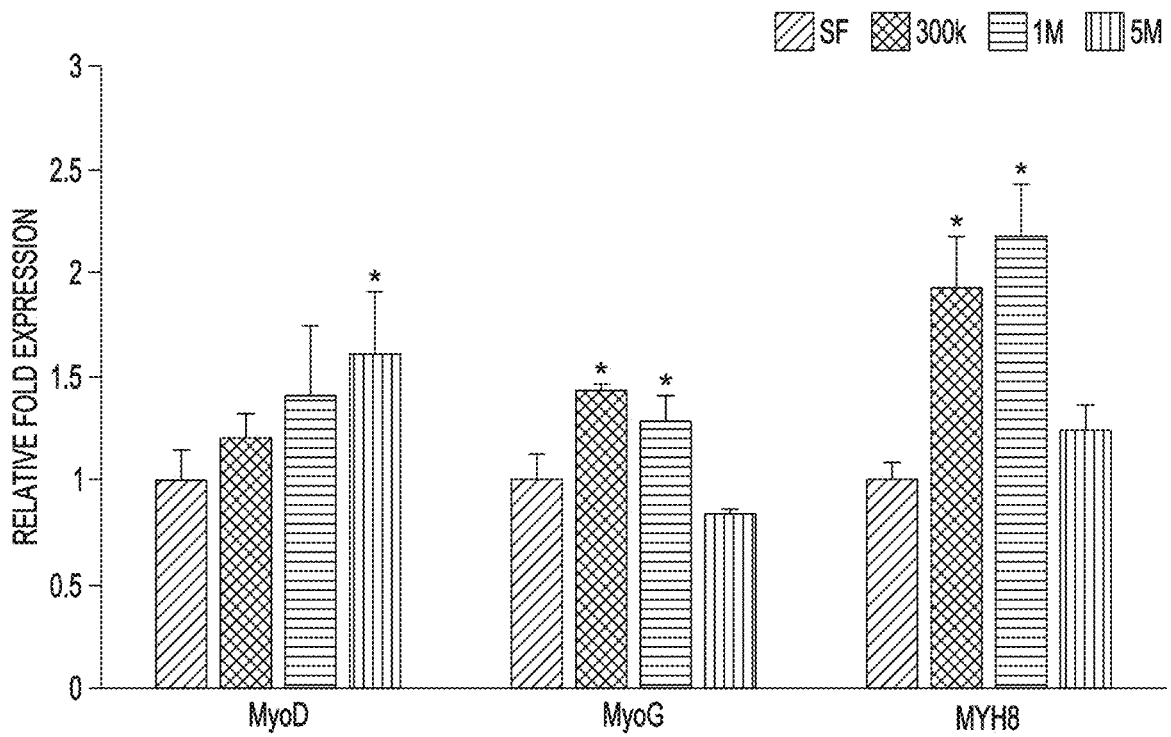
FIG. 3C illustrates gene expression analysis by qPCR demonstrating a significant increase in myoblast differentiation markers in myoblasts cultured with 300 k and 1M cell secretome compared to SF, whereas no significant changes in differentiation markers were observed for myoblasts cultured with 5M cell secretome compared to SF ($*p<0.05$), in accordance with various embodiments.
Figure 3D:
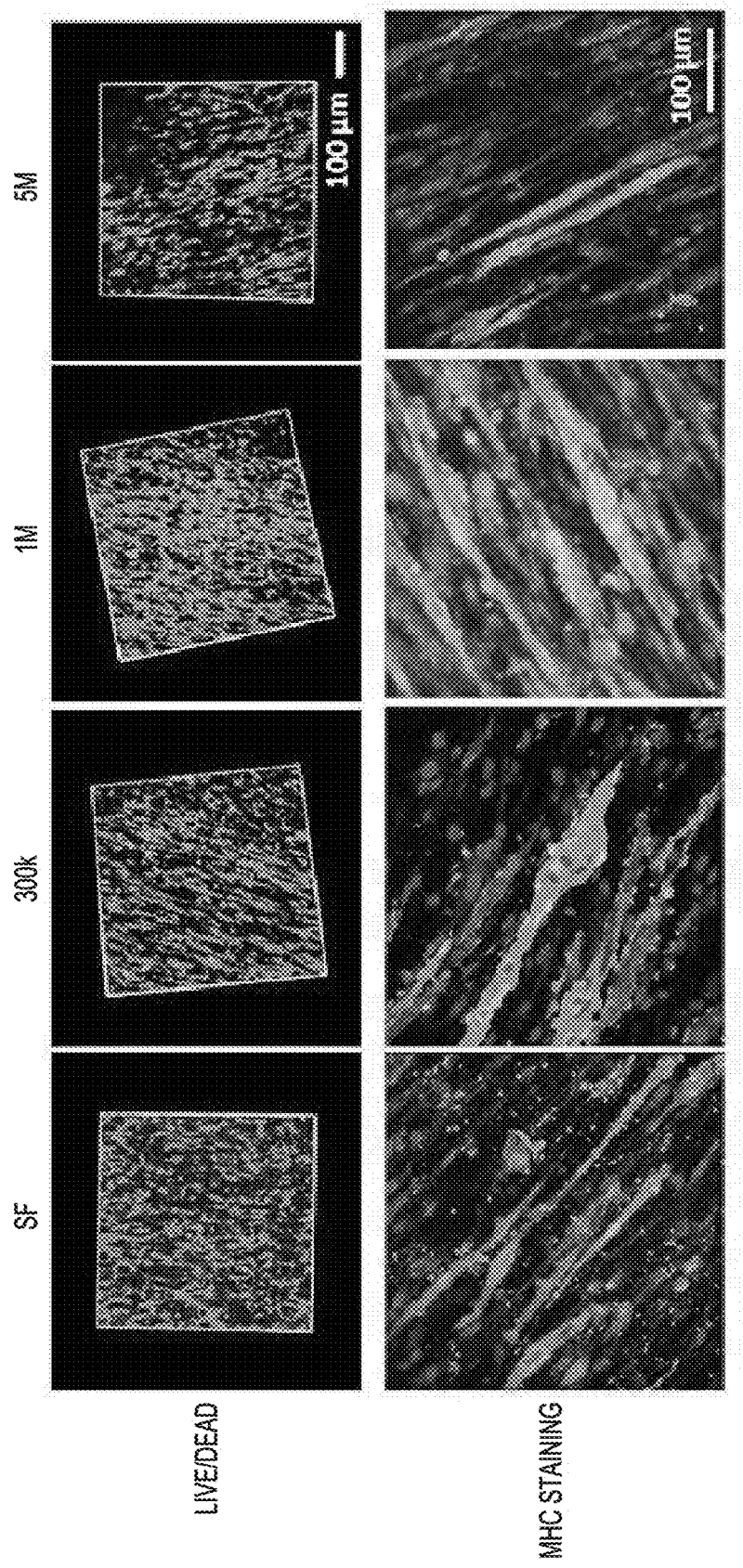
Figure 4:
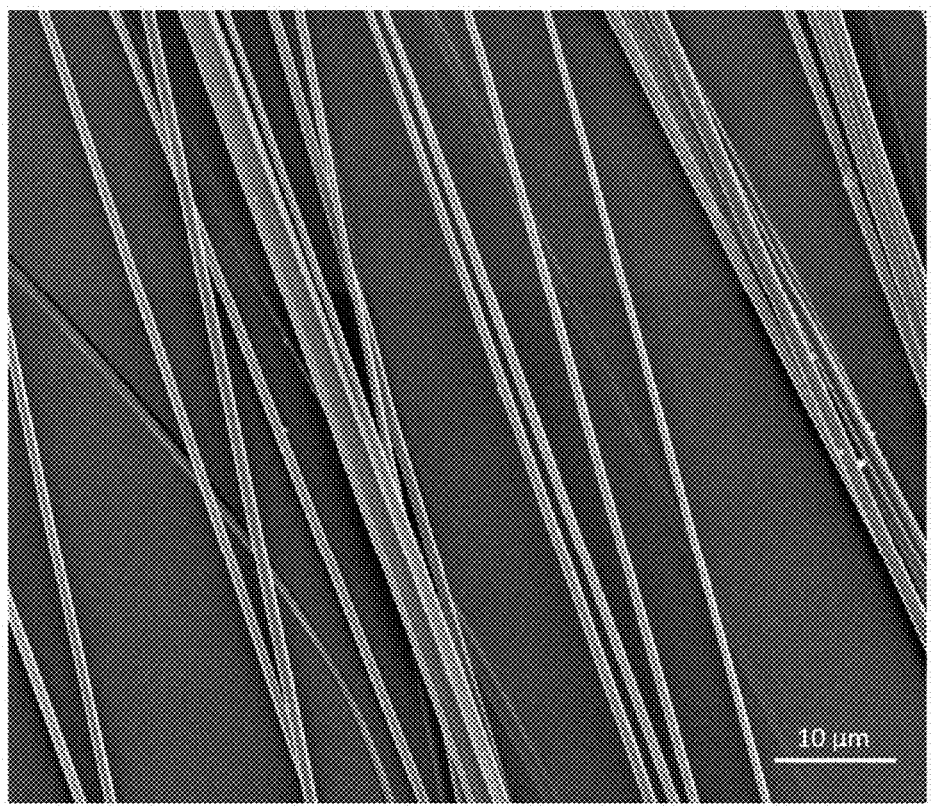
FIG. 4 illustrates a representative SEM micrograph showing the aligned PLGA electrospun fibers, in accordance with various embodiments.
Figure 5A:
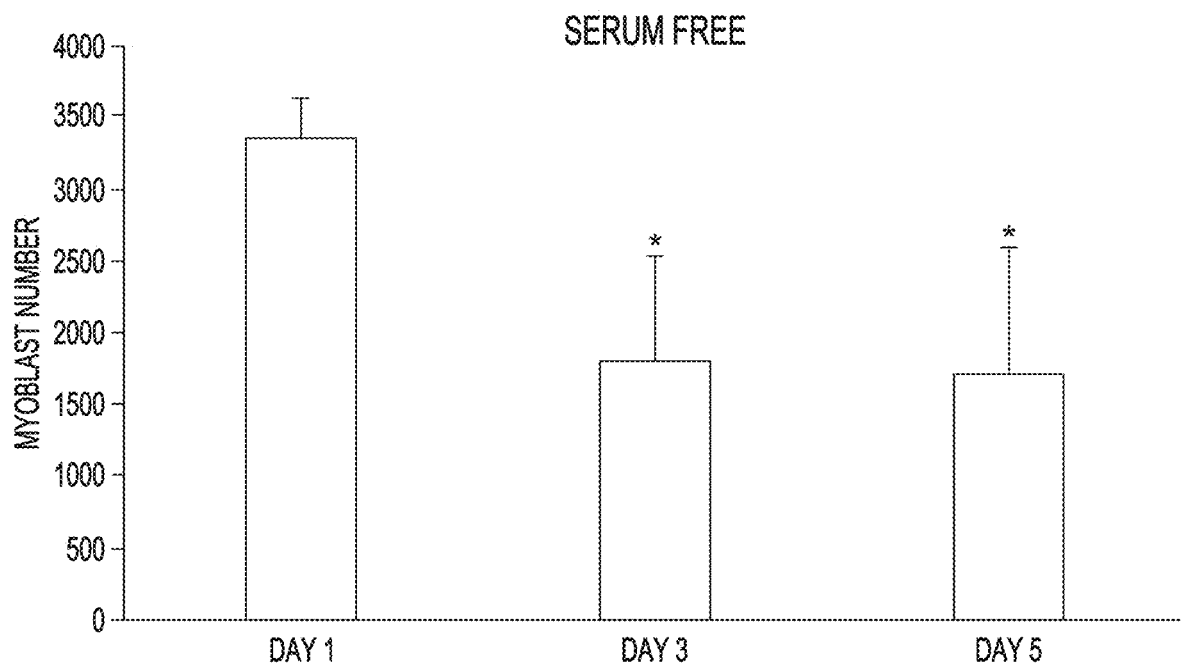
FIG. 5A illustrates an MTS assay showing changes of myoblast cell numbers on 3D aligned electrospun fiber scaffold during culture with SF, in accordance with various embodiments.
Figure 5B:
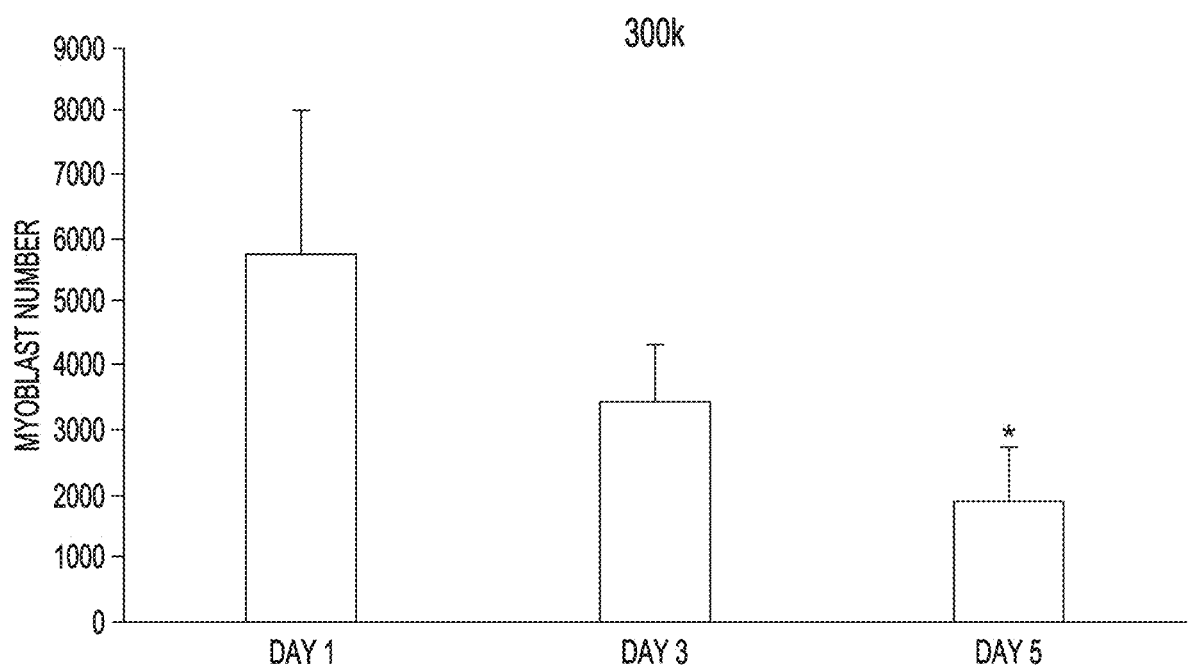
FIG. 5B illustrates an MTS assay showing changes of myoblast cell numbers on 3D aligned electrospun fiber scaffold during culture with secretome obtained from the 300 k group, in accordance with various embodiments.
Figure 5C:
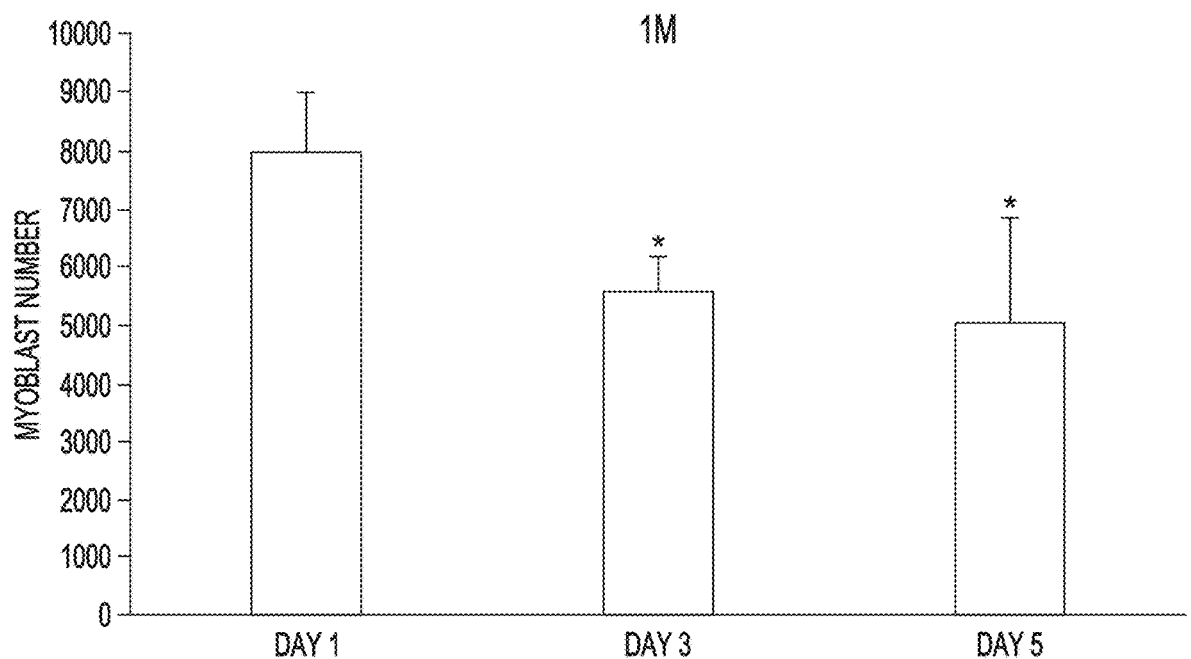
FIG. 5C illustrates an MTS assay showing changes of myoblast cell numbers on 3D aligned electrospun fiber scaffold during culture with secretome obtained from the 1M group, in accordance with various embodiments.
Figure 5D:
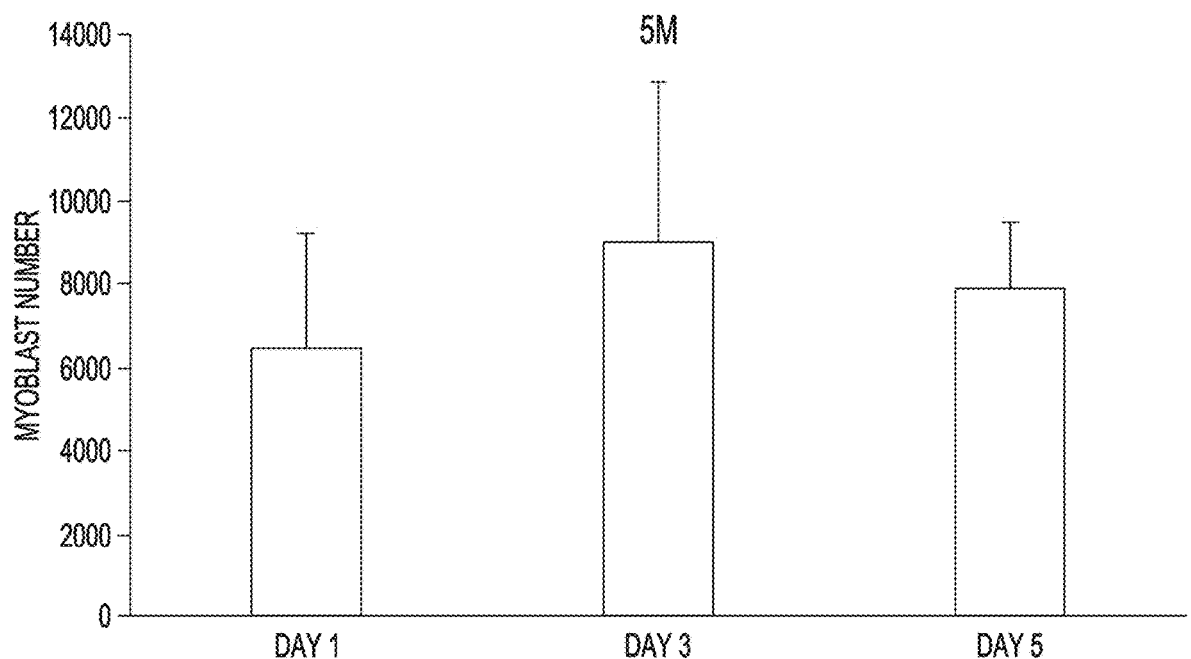
FIG. 5D illustrates an MTS assay showing changes of myoblast cell numbers on 3D aligned electrospun fiber scaffold during culture with secretome obtained from the 5M group, in accordance with various embodiments.

PC12 secretome treatment on myoblasts with 3D culture: To evaluate the effects of PC12 secretome treatment on myoblasts in 3D culture, we seeded myoblasts on aligned, electrospun PLGA fiber scaffolds (fiber diameter ~3 µm), which have been previously optimized to mimic the anisotropic organization of skeletal muscle ECM for myoblast culture. FIG. 3A shows schematics illustrating the treatment of myoblasts on 3D aligned electrospun fiber scaffold with the PC12-derived secretome. FIG. 4 illustrates a representative SEM micrograph showing the aligned PLGA electrospun fibers. Similar to our findings with 2D culture, myoblasts treated with secretome obtained from 1M and 5M showed a significant increase in metabolic activity as compared to those treated with SF and secretome obtained from 300 k at day 3 and day 5, as shown in FIG. 3B. Furthermore, while serum starvation resulted in a significant decrease in cell numbers during culture, treatment with secretome obtained from 5M sustained numbers of myoblasts as indicated by the MTS assay. FIG. 5A illustrates an MTS assay showing changes of myoblast cell numbers on 3D aligned electrospun fiber scaffold during culture with SF. FIG. 5B illustrates an MTS assay showing changes of myoblast cell numbers on 3D aligned electrospun fiber scaffold during culture with secretome obtained from the 300 k group. FIG. 5C illustrates an MTS assay showing changes of myoblast cell numbers on 3D aligned electrospun fiber scaffold during culture with secretome obtained from the 1M group. FIG. 5D illustrates an MTS assay showing changes of myoblast cell numbers on 3D aligned electrospun fiber scaffold during culture with secretome obtained from the 5M group. A significant decrease in cell number was observed on treatment with SF, secretome obtained from the 300 k group, and secretome obtained from the 1M group. However, no significant changes in cell number were observed on treatment with secretome obtained from the 5M group. FIG. 5E-H illustrate representative confocal micrographs of live/dead assay at day 5 for myoblasts treated with (5E) SF, (5F) secretome obtained from the 300 k group, (5G) secretome obtained from the 1M group, and (5H) secretome obtained from the 5M group. This was in line with the beneficial effects of secretome on myoblast proliferation observed with 2D TCPS culture. Confocal micrographs of live/dead staining also confirmed higher viability of myoblasts in secretome obtained from 5M as compared to SF, secretome obtained from 300 k and 1M, as shown in FIGS. 3D and 5A-H. After 4 days of differentiation, gene expression of MyoG and MYH8 was upregulated for myoblasts treated with secretome obtained from 300 k and 1M as compared to those treated with SF. No significant changes in expression of MyoG and MYH8 were observed for myoblasts treated with secretome obtained from 5M as compared to those treated with SF. Confocal micrographs with immunofluorescent staining for MHC confirmed enhanced differentiation for myoblasts treated with secretome obtained from 300 k and 1M (FIG. 3D). Taken together, both 2D and 3D culture results suggested that PC12 secretome modulated myoblast behavior in a dose-dependent manner, with the higher secretome concentration (5M) promoting proliferation and lower secretome concentration (300 k) enhancing myoblast differentiation.

Figure 6A:
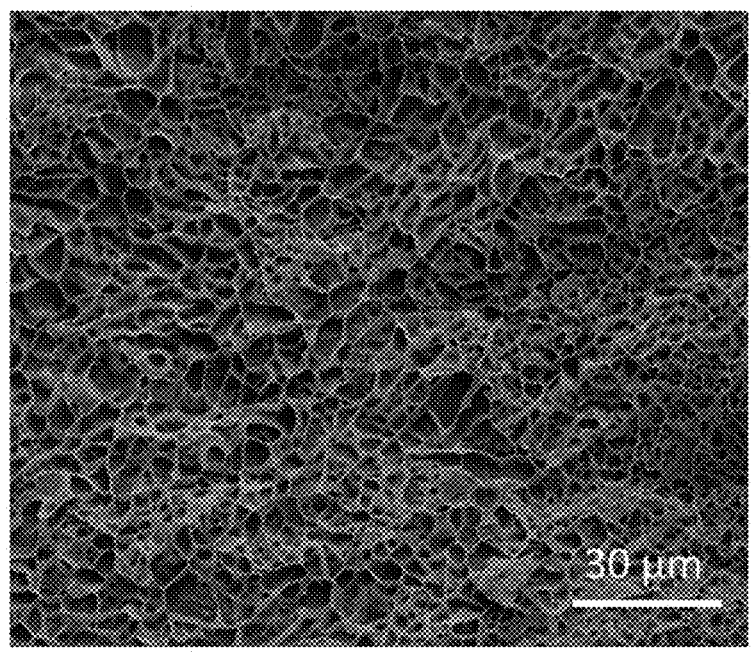
FIGS. 6A-B illustrate representative SEM micrographs of HCP hydrogels, in accordance with various embodiments.
Figure 6B:
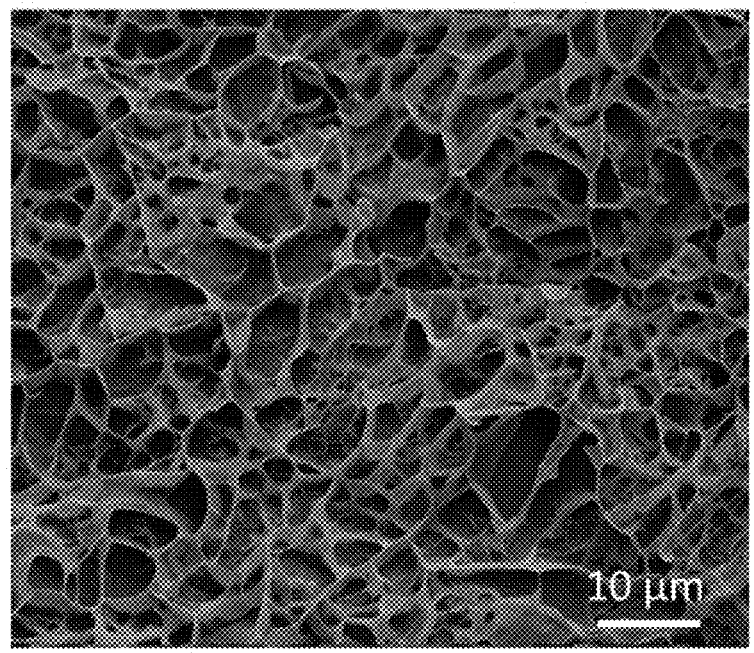
Figure 7A:
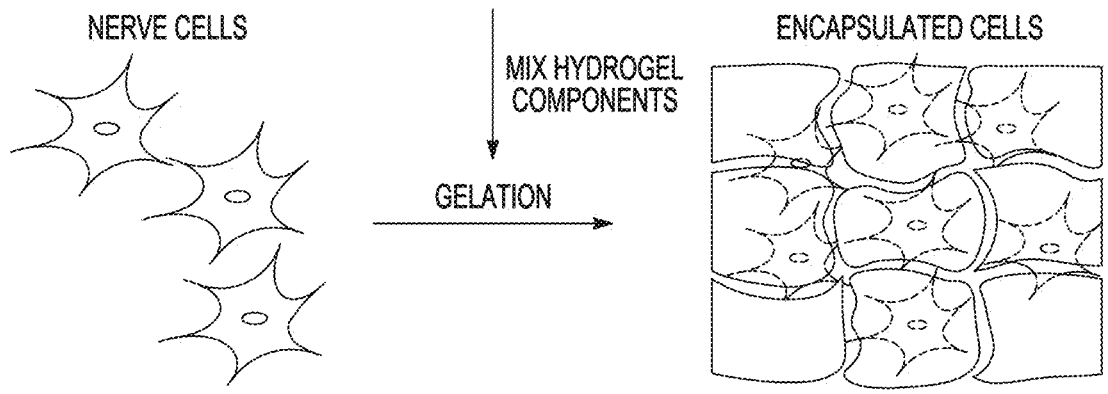
FIG. 7A shows schematics illustrating the encapsulation of PC12 cells in HCP hydrogels. (B) MTS assay demonstrating an increase in metabolic activity of PC12 cells encapsulated with different cell densities in hydrogels over time, indicating the ability of HCP hydrogels to support cell growth ($*p<0.05$), in accordance with various embodiments.
Figure 7B:
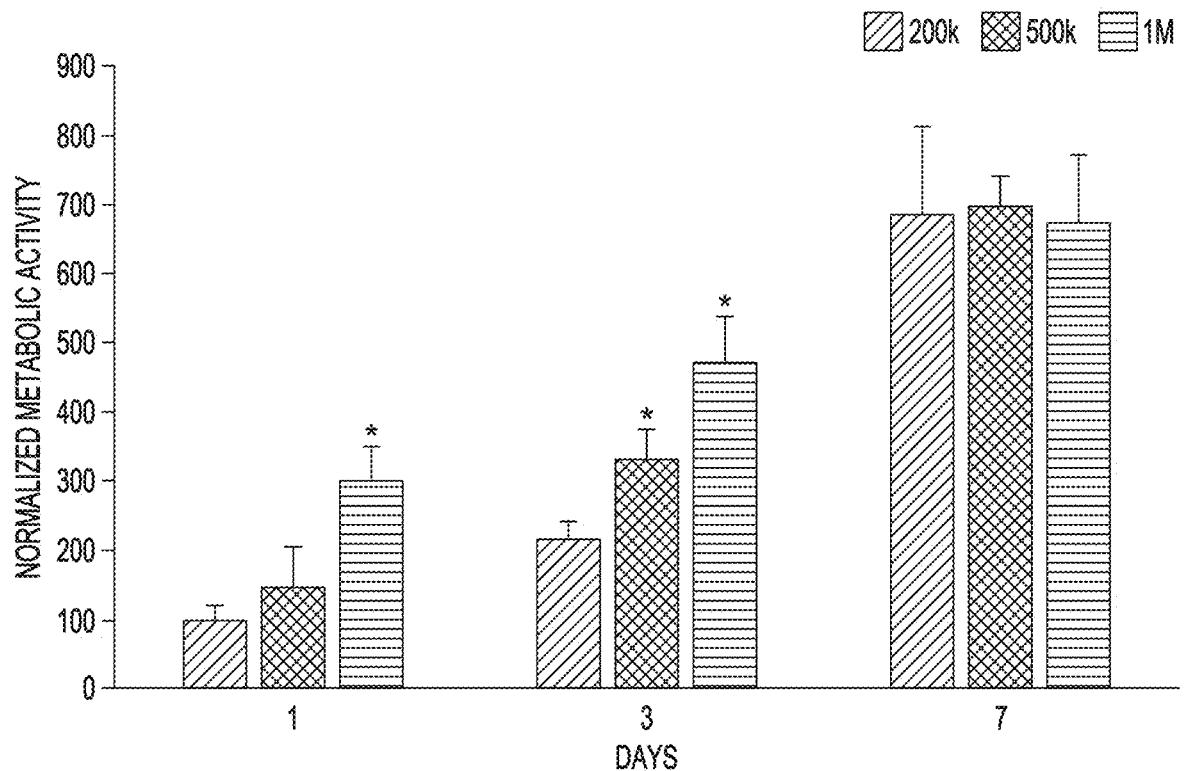
FIG. 7B illustrates MTS assay demonstrating an increase in metabolic activity of PC12 cells encapsulated with different cell densities in hydrogels over time, indicating the ability of HCP hydrogels to support cell growth ($*p<0.05$), in accordance with various embodiments.
Figure 7C:
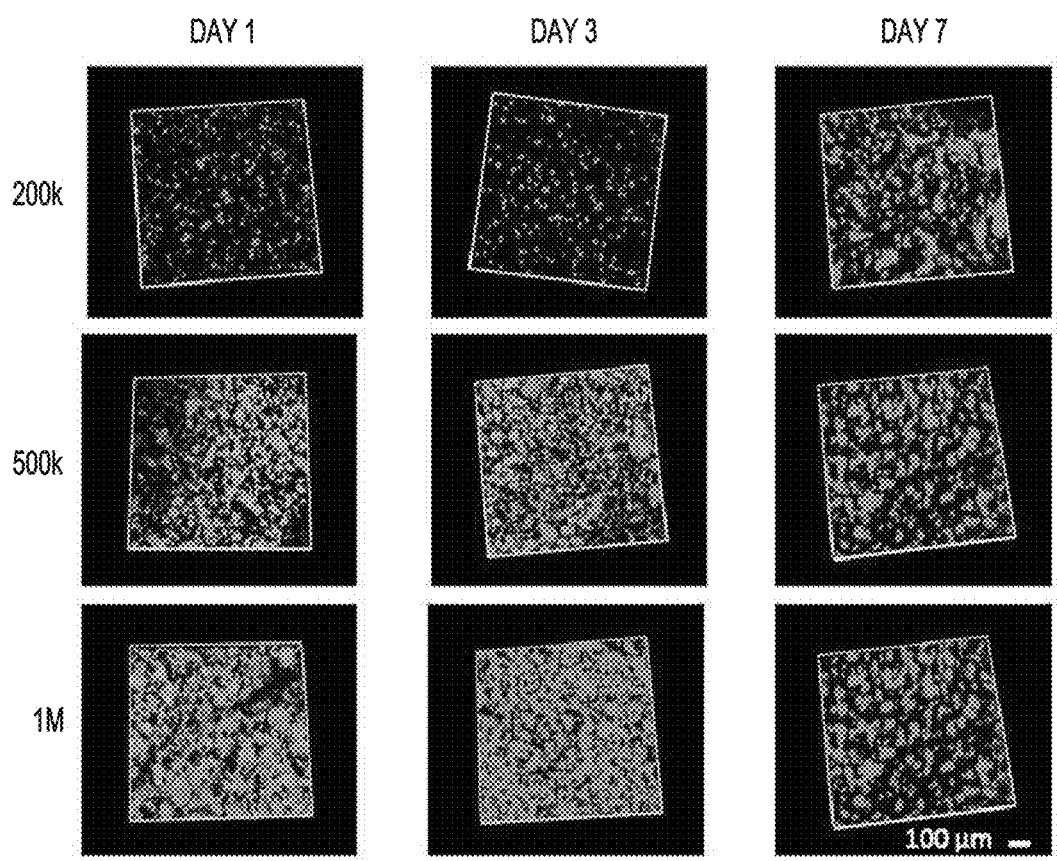
FIG. 7C illustrates live/dead assay showing viability of cells encapsulated in hydrogels with 200 k (top row), 500 k (middle row), and 1M cells (bottom row) at day 1, 3 and 7, in accordance with various embodiments.
Figure 7D:
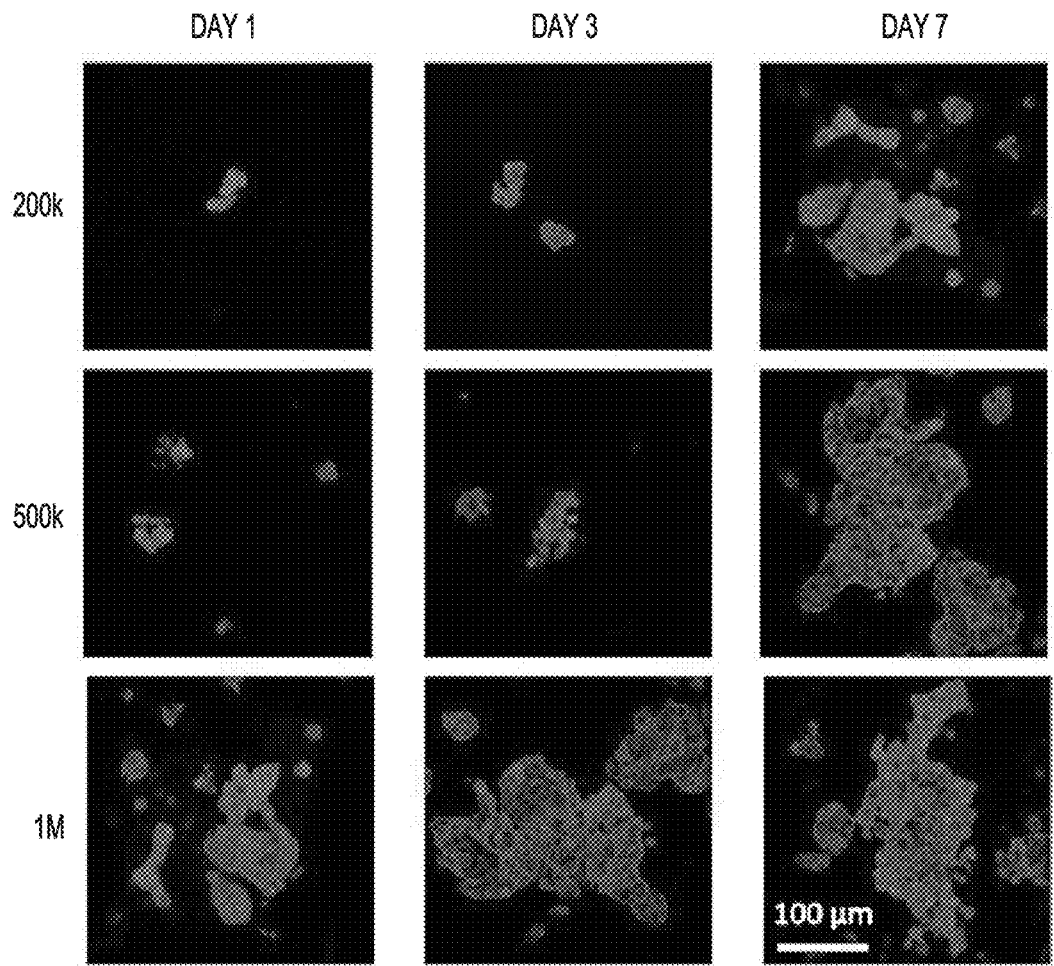
FIG. 7D illustrates confocal micrographs by actin staining showing aggregation of PC12 cells during culture at 200 k (top row), 500 k (middle row), and 1M (bottom row) cell densities, in accordance with various embodiments. Red indicates actin, and blue indicates nuclei.
Figure 8A:
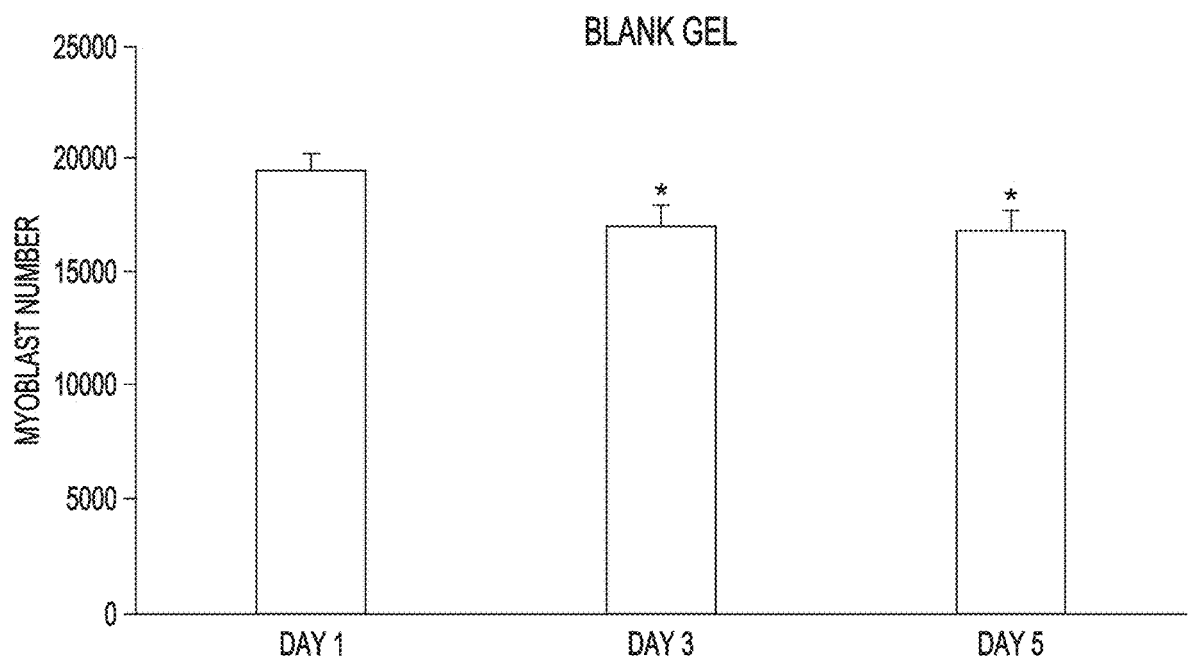
FIG. 8A illustrates an MTS assay showing changes of myoblast cell numbers over time in the co-culture setup when treated with blank hydrogels, in accordance with various embodiments.
Figure 8B:
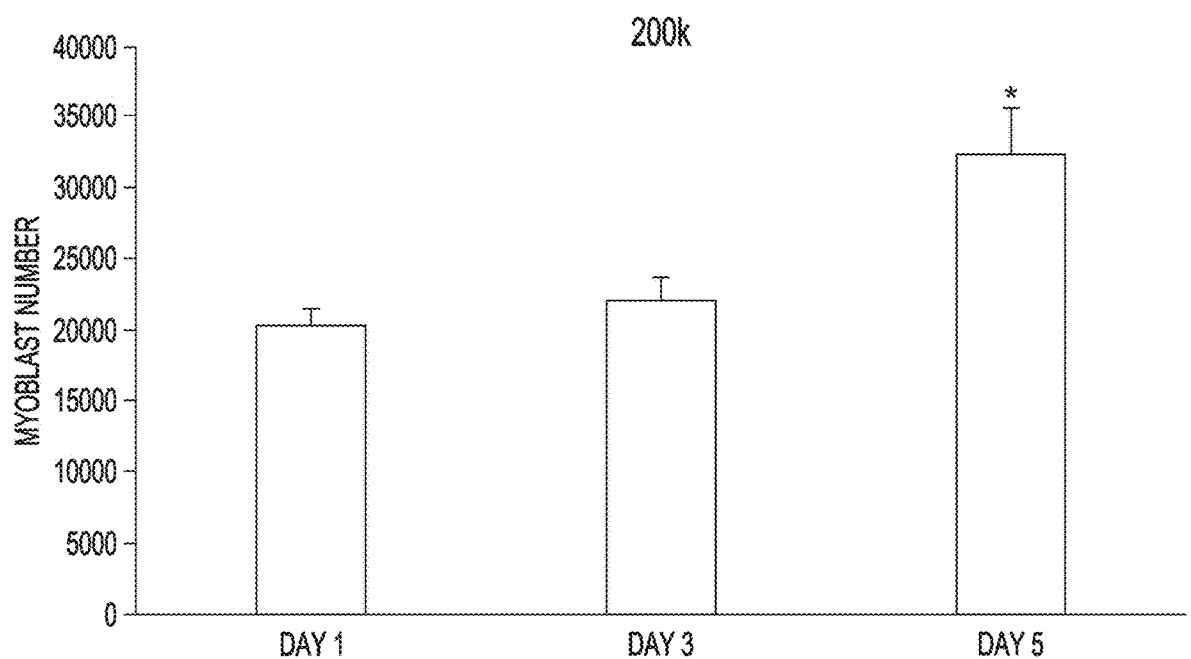
FIG. 8B illustrates an MTS assay showing changes of myoblast cell numbers over time in the co-culture setup when treated with hydrogels encapsulating 200 k cells, in accordance with various embodiments.
Figure 8C:
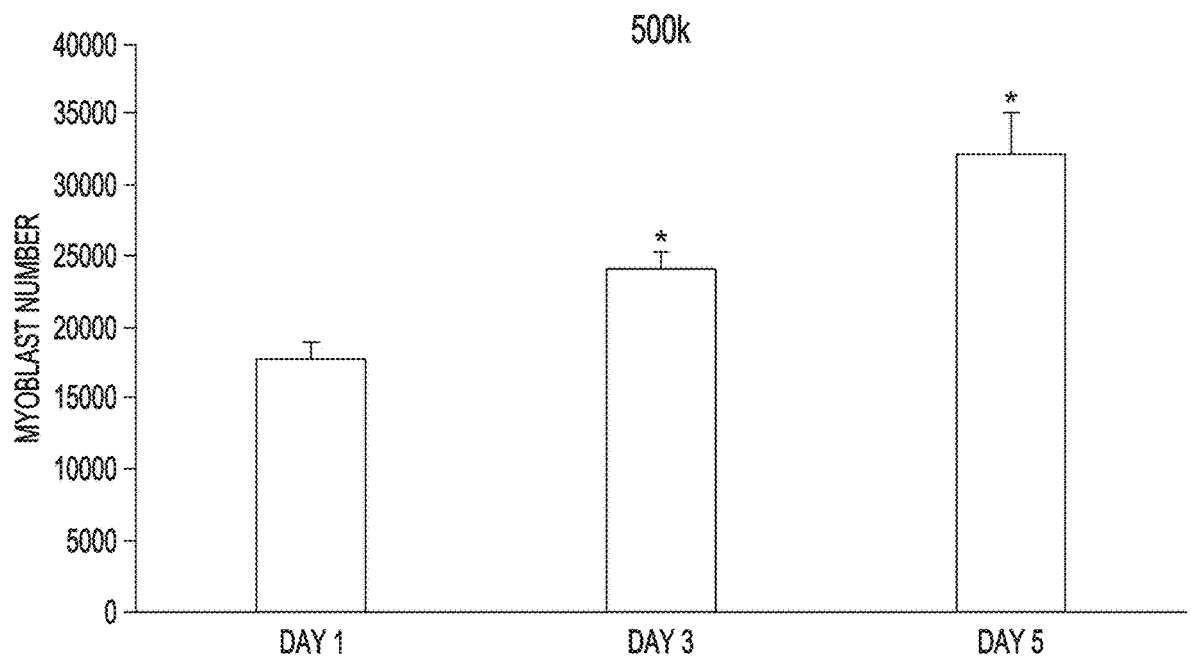
FIG. 8C illustrates an MTS assay showing changes of myoblast cell numbers over time in the co-culture setup when treated with hydrogels encapsulating 500 k cells, in accordance with various embodiments.
Figure 8D:
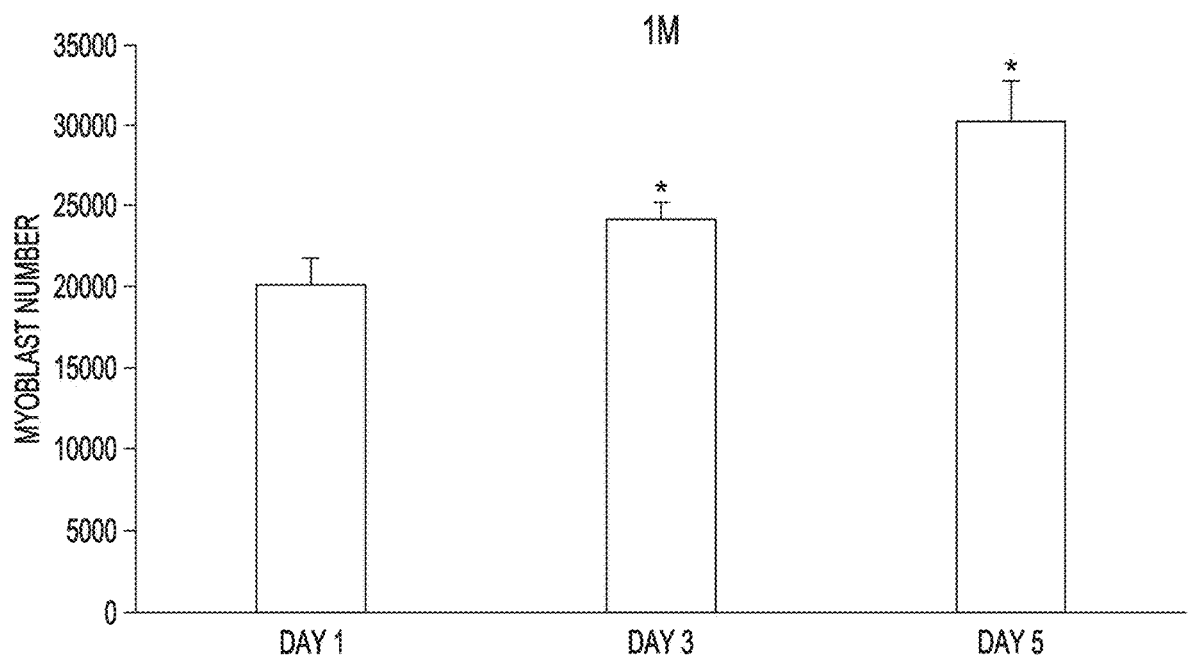
FIG. 8D illustrates an MTS assay showing changes of myoblast cell numbers over time in the co-culture setup when treated with hydrogels encapsulating 1M cells, in accordance with various embodiments.

PC12 encapsulation in HCP hydrogels: The formation of hydrogel was confirmed using the vial-tilting method. Rheology characterization with time sweep analysis showed that the HCP hydrogels had a storage modulus G' of 13.0±1.8 kPa, which recapitulates the elasticity of muscle. The formed HA-CS hydrogels exhibited a well-defined, porous structure as evidenced from cryo-SEM micrographs (as shown in FIGS. 6A-B), which is desirable to enable diffusion and delivery of secretome factors secreted by PC12 cells. FIGS. 6A and 6B illustrate representative SEM micrographs of HCP hydrogels, with FIG. 6A showing a lower magnification micrograph than FIG. 6B. The controlled gelation process enabled in situ 3D encapsulation of PC12 cells with high viability. FIG. 7A shows schematics illustrating the encapsulation of PC12 cells in HCP hydrogels. (B) MTS assay demonstrating an increase in metabolic activity of PC12 cells encapsulated with different cell densities in hydrogels over time, indicating the ability of HCP hydrogels to support cell growth (*p<0.05). Three cell densities, namely 200 k, 500 k and 1M cells per hydrogel, were used to retain cell number to culture media volume ratios comparable to that of secretome obtained from 5M cells. HCP hydrogels supported PC12 growth as evidenced by the increase in metabolic activity of the cells and maintained cell viability over time, as shown in FIGS. 7B-C and 8A-D. FIG. 7B illustrates MTS assay demonstrating an increase in metabolic activity of PC12 cells encapsulated with different cell densities in hydrogels over time, indicating the ability of HCP hydrogels to support cell growth (*p<0.05). FIG. 7C illustrates live/dead assay showing viability of cells encapsulated in hydrogels with 200 k (top row), 500 k (middle row), and 1M cells (bottom row) at day 1, 3 and 7. FIG. 8A illustrates an MTS assay showing changes of myoblast cell numbers over time in the co-culture setup when treated with blank hydrogels. FIG. 8B illustrates an MTS assay showing changes of myoblast cell numbers over time in the co-culture setup when treated with hydrogels encapsulating 200 k cells. FIG. 8C illustrates an MTS assay showing changes of myoblast cell numbers over time in the co-culture setup when treated with hydrogels encapsulating 500 k cells. FIG. 8D illustrates an MTS assay showing changes of myoblast cell numbers over time in the co-culture setup when treated with hydrogels encapsulating 1M cells. A significant increase in myoblast cell number was observed when co-cultured with PC12-encapsulated hydrogels. Furthermore, there was a significant difference in metabolic activities of 500 k and 1M cells as compared to 200 k cells at day 3. However, no significant differences among the groups were observed at day 7, indicating that cell density plateaued within the hydrogel matrix. In addition, actin cytoskeleton staining of the encapsulated cells revealed cell aggregation resulting from cell density increases after 7 days of culture, as shown in FIG. 7D. FIG. 7D illustrates confocal micrographs by actin staining showing aggregation of PC12 cells during culture at 200 k (top row), 500 k (middle row), and 1M (bottom row) cell densities. Red indicates actin and blue indicates nuclei.

Figure 9A:
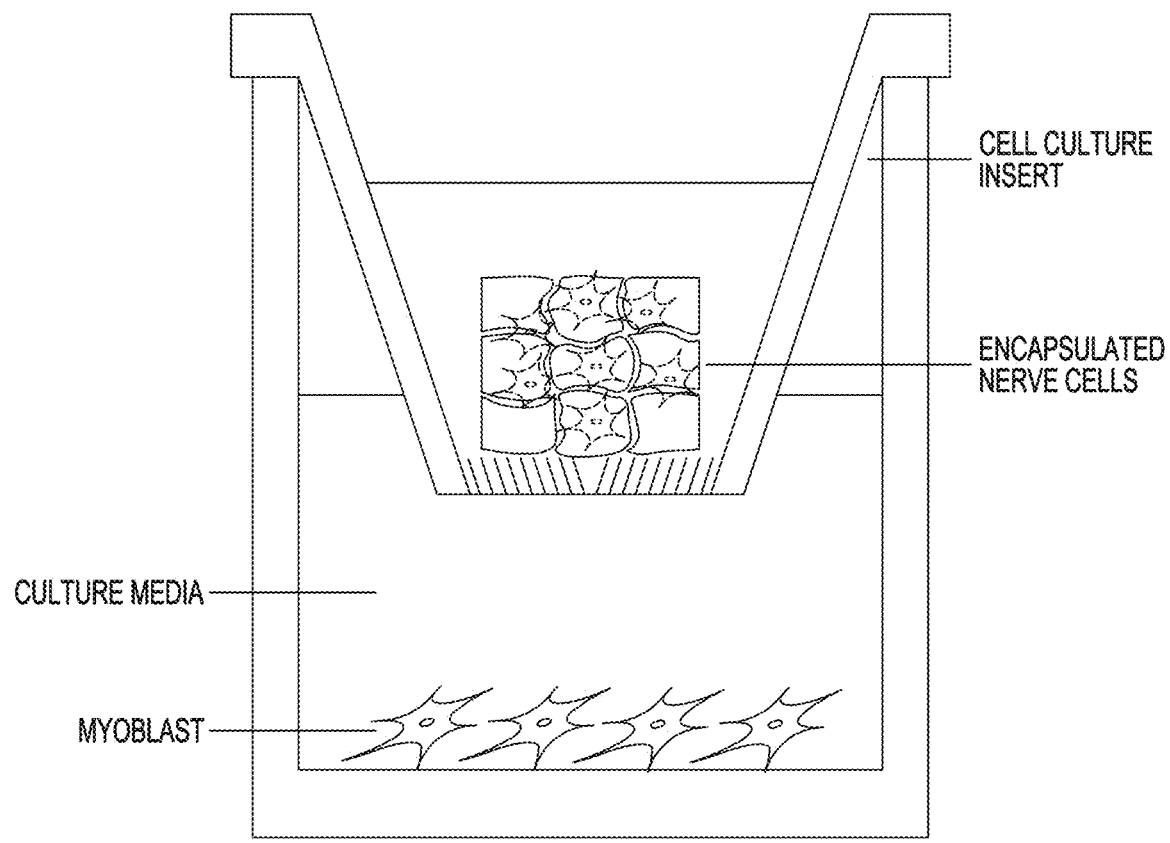
FIG. 9A shows schematics illustrating the transwell co-culture setup, in accordance with various embodiments.
Figure 9B:
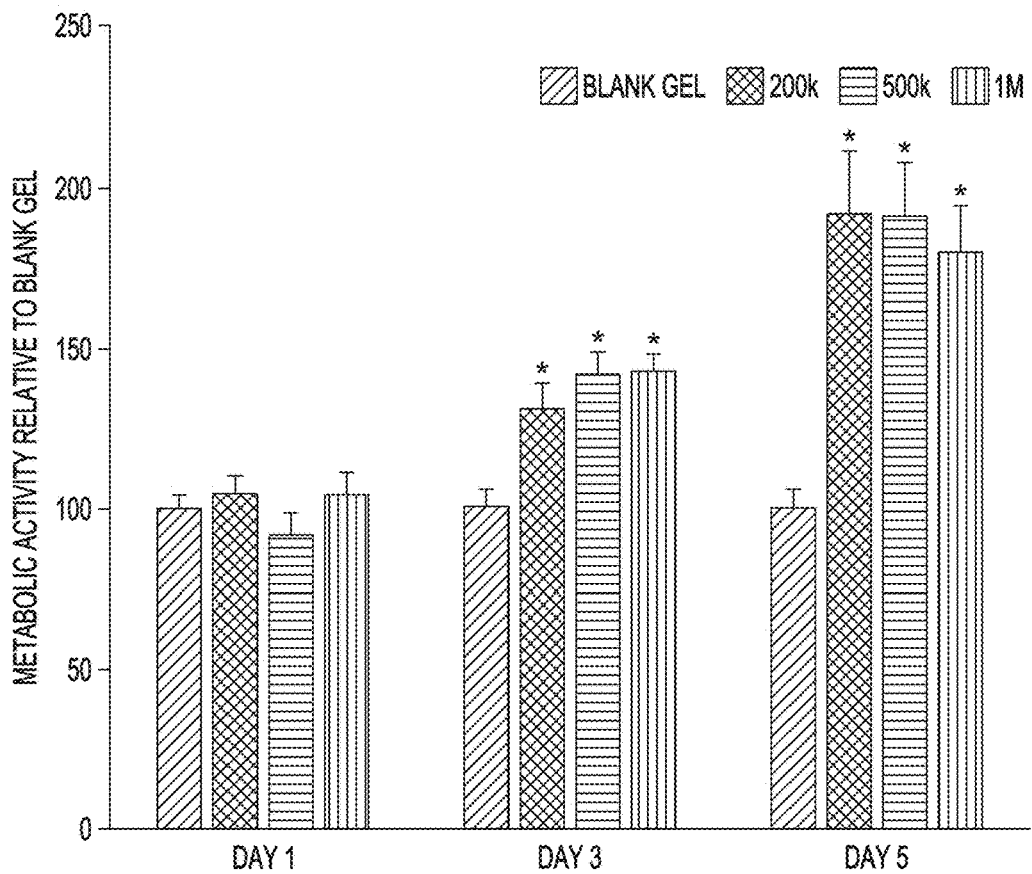
FIG. 9B illustrates an MTS assay demonstrating a significant increase in metabolic activity of myoblasts over time when co-cultured with HCP hydrogels encapsulating PC12 cells at three different densities namely 200 k, 500 k, and 1M ($*p<0.05$), in accordance with various embodiments.
Figure 10:
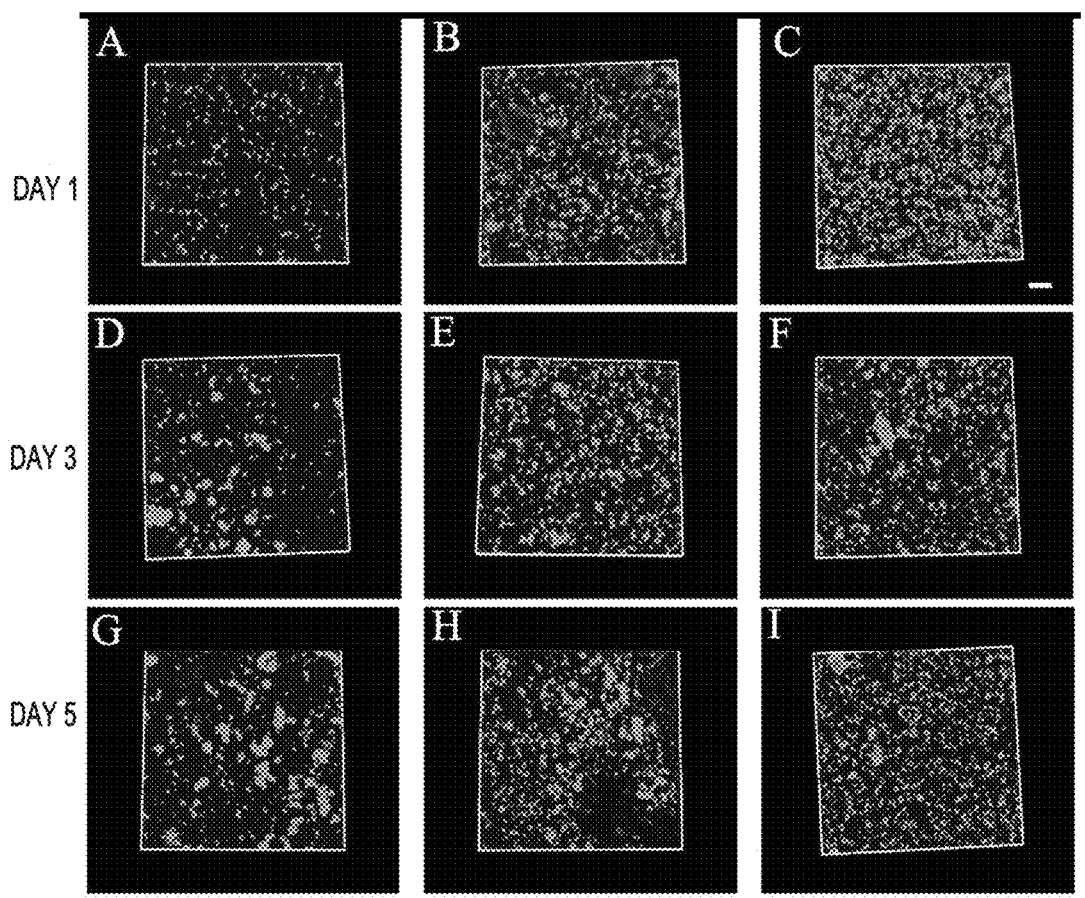
FIG. 10 illustrate representative confocal micrographs of live/dead assay of hydrogels encapsulating 200 k, 500 k, and 1M PC12 cells in the co-culture study at (top row) day 1. (middle row) day 3, and (bottom row) day 5, in accordance with various embodiments.

Co-culture transwell study: To further assess the effects of PC12 secretome on myoblasts in situ, a co-culture transwell system was set up as shown in FIG. 9A. During co-culture, there was a significant increase in metabolic activities of myoblasts co-cultured with PC12 cells of all densities compared to blank gel at day 3 and day 5, as shown in FIG. 9B). Furthermore, a significant increase in myoblast number from day 1 to day 5 was observed when co-cultured with PC12 cells compared to blank gel (as shown in FIGS. 8A-D). Additionally, confocal micrographs by live/dead assay showed that the PC12 cells encapsulated in the hydrogel maintained high viability during cell culture (as shown in FIG. 10), which is important for sustained secretion of signaling factors. FIG. 10 illustrates representative confocal micrographs of live/dead assay of hydrogels encapsulating 200 k, 500 k, and 1M PC12 cells in the co-culture study at (top row) day 1. (middle row) day 3, and (bottom row) day 5.

Figure 9C:
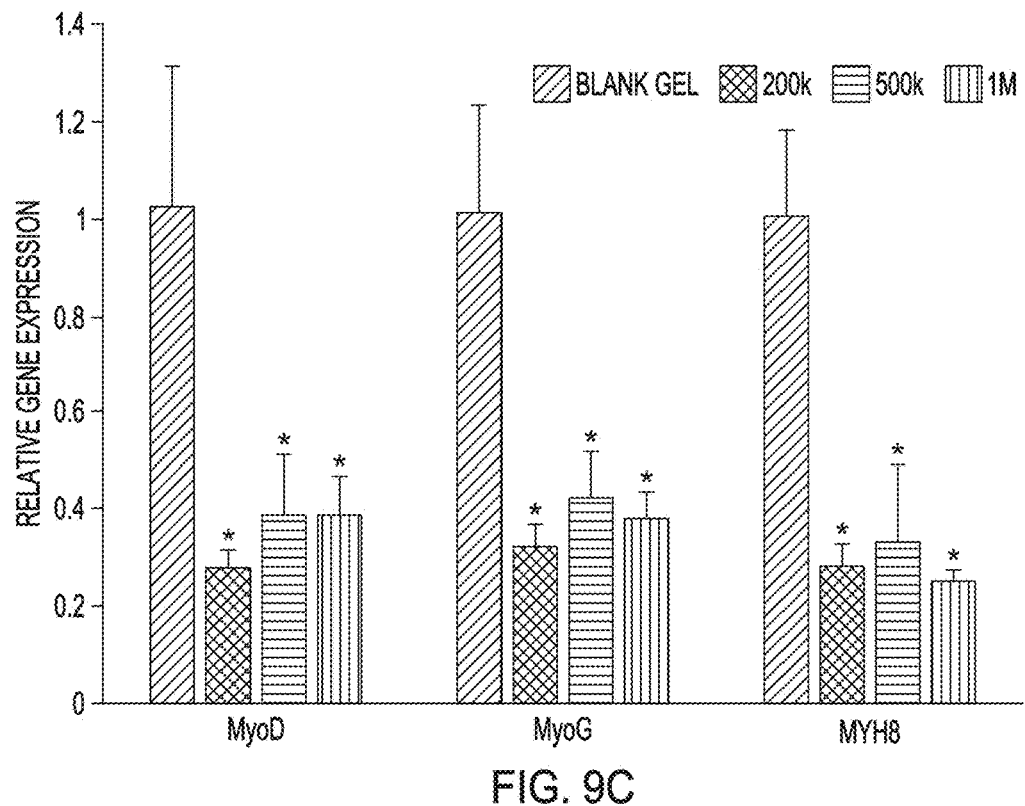
FIG. 9C illustrates gene expression analysis by qPCR demonstrating a reduced gene expression of myoblast differentiation markers in the co-culture setup ($*p<0.05$), in accordance with various embodiments.
Figure 9D:
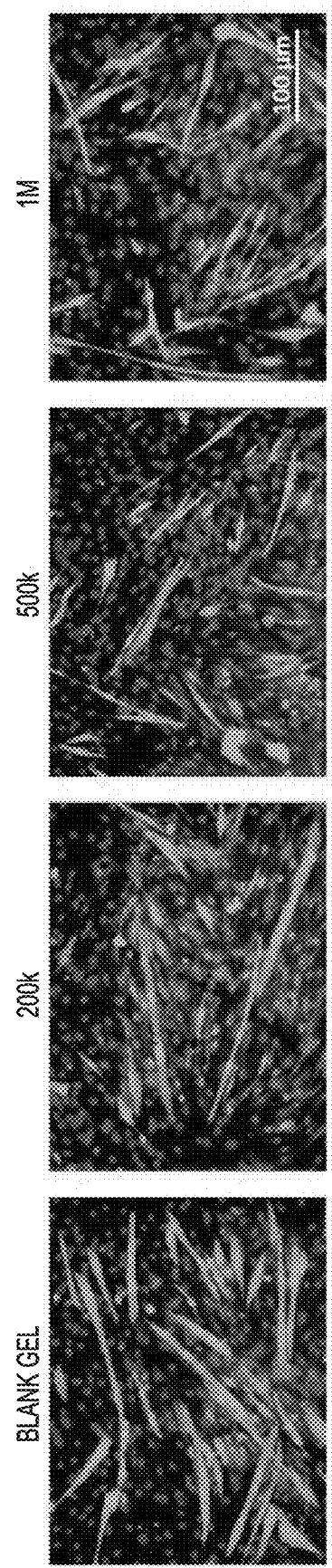
FIG. 9D illustrates fluorescent micrographs by immunofluorescent staining for MHC showing less organized myotube formation for C2C12 cells co-cultured with PC12 cells as compared to those co-cultured with blank gel, in accordance with various embodiments. Green indicates MHC, and blue indicates nuclei.

After 4 days of differentiation, C2C12 cells co-cultured with PC12 cells showed a significant decrease in gene expression of differentiation markers MyoD. MyoG, and MYH8 as compared to those co-cultured with blank gel (FIG. 9C). Consistently, immunofluorescent staining for MHC revealed a less-organized myotube formation for C2C12 cells co-cultured with PC12 cells as compared to those co-cultured with blank gel (FIG. 9C). These results corroborated well with the previous results obtained from 5M secretome studies in both 2D and 3D cultures, and it demonstrated feasibility of using HCP hydrogel encapsulation to harness effects of in situ nerve cell secreted factors on myoblasts.

Figure 11A:
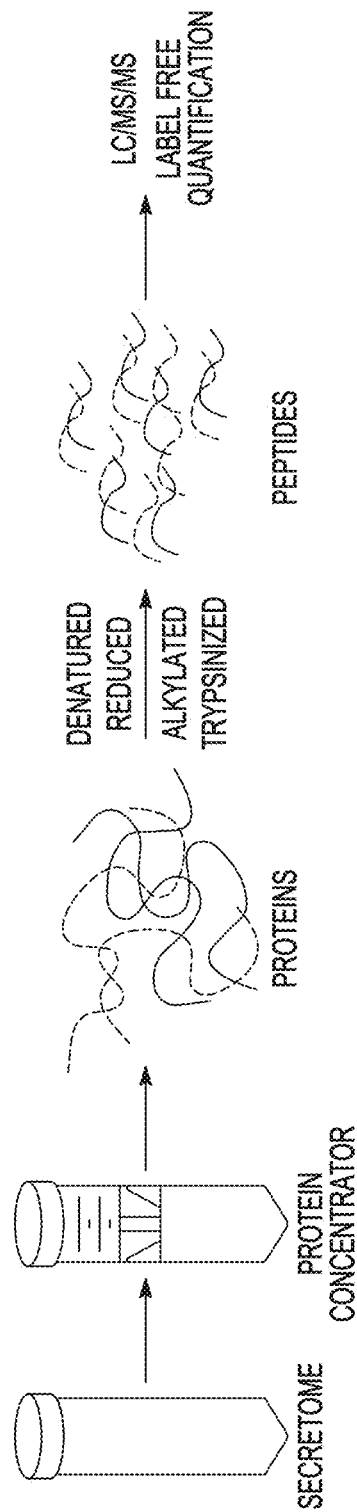
FIG. 11A shows schematics illustrating the overall process of proteomics to analyze the secretome obtained from PC12 cells, in accordance with various embodiments.
Figure 11B:
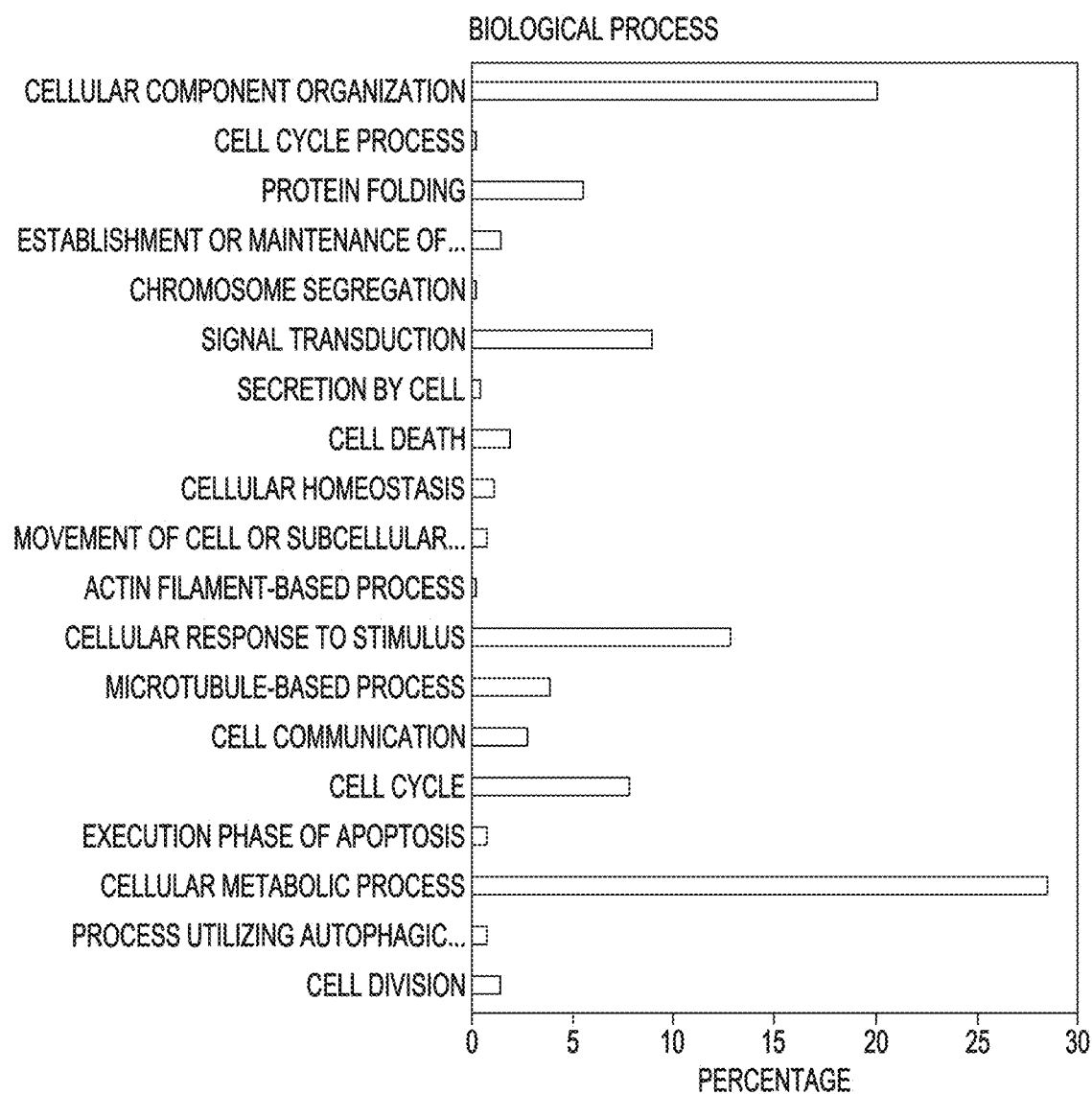
FIG. 11B illustrates a bar chart showing GO Biological process annotation of nerve cell secretome using the PANTHER database, in accordance with various embodiments.
Figure 11C:
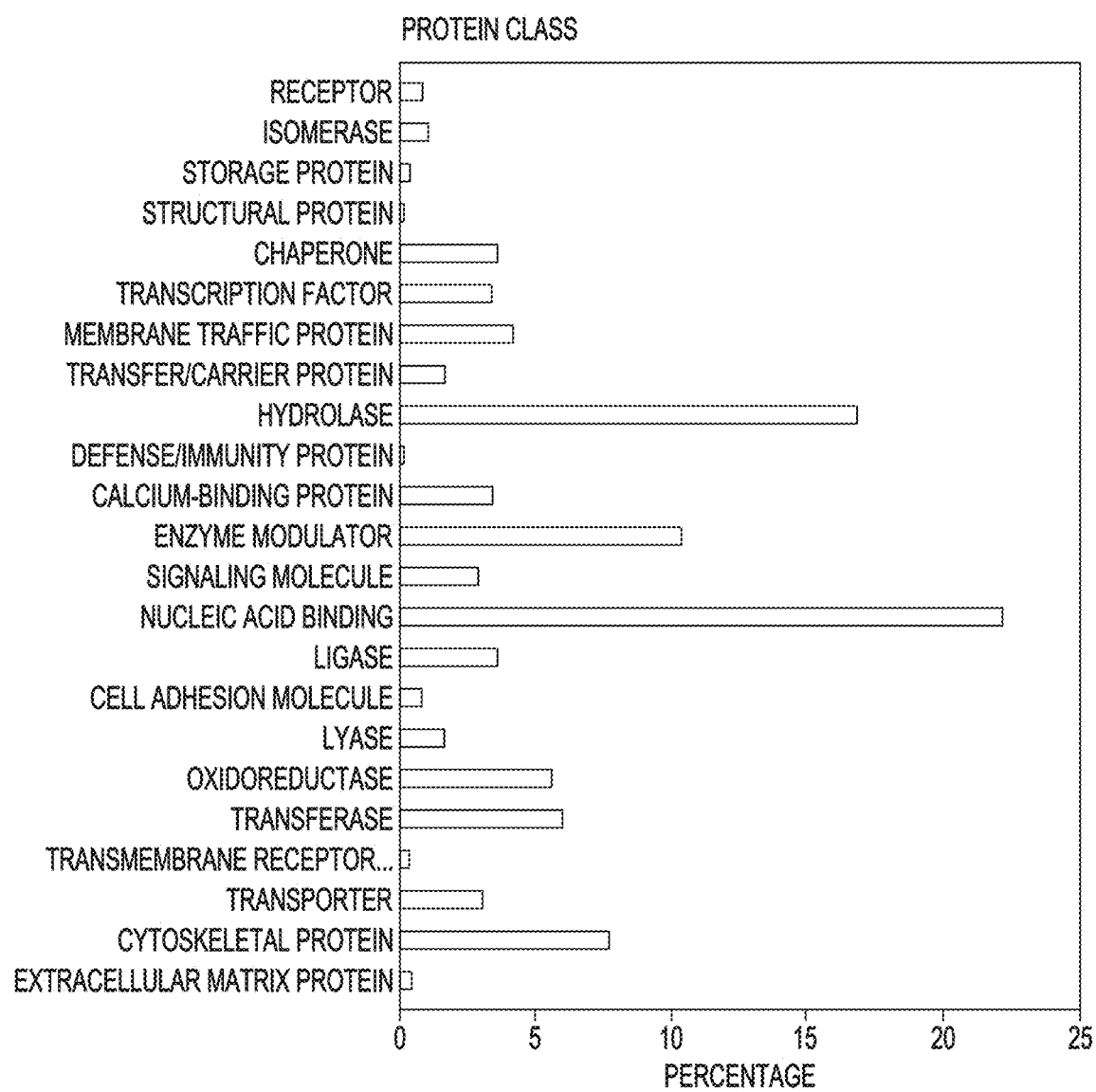
FIG. 11C illustrates a bar chart demonstrating protein class annotation of nerve cell secretome using Panther database, in accordance with various embodiments.
Figure 12:
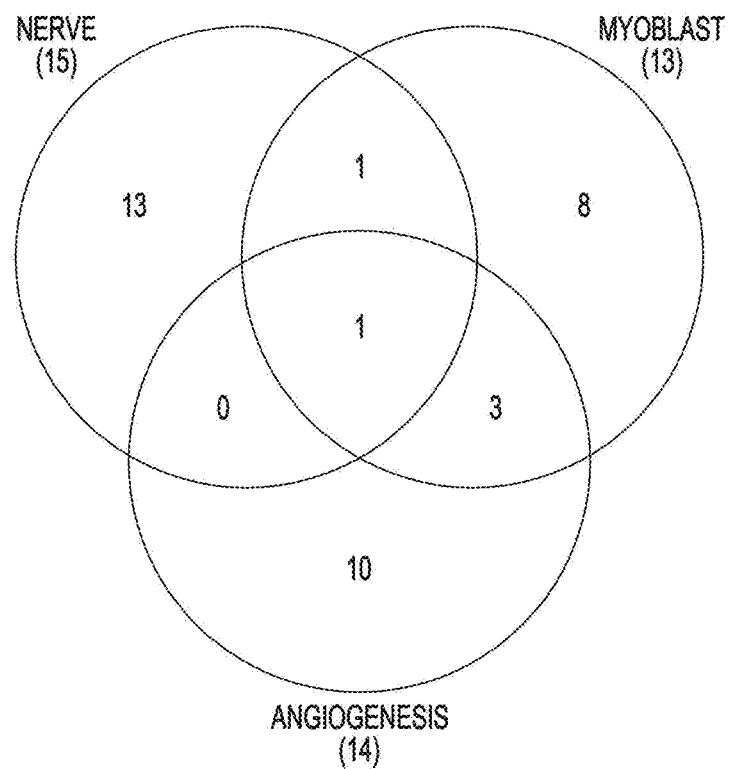
FIG. 12 illustrates a Venn-diagram illustrating the interactions of proteins annotated with roles in muscle, nerves and angiogenesis, in accordance with various embodiments.

Proteomics characterization of PC12 secretome: Our preliminary results demonstrated that nerve cells secreted signaling factors that modulated myoblast behavior. For therapeutic application, it is critical to choose conditions where the factors induce myoblast proliferation and survival, as they play an important role in skeletal muscle regeneration. In this study, secretome obtained from 5M induced proliferation and survival of myoblasts in 2D and 3D culture conditions. Therefore, we chose to analyze and characterize secretome obtained from 5M for potential therapeutics. To this end, we comprehensively detected and evaluated secreted proteins using label free LC/MS/MS technique as shown in FIG. 11A. To avoid contamination and complexity from the serum. SF conditioned media was collected and analyzed. A total of 2088 protein/peptides were identified from the secretome of 5M using the MaxQuant search engine. The peptide count was filtered based on the MS/MS counts, and proteins with MS/MS count of greater than 2 were processed for further analysis. Additionally, proteins with minimum of 2 peptide counts and proteins with minimum of two LFQ intensity entries (2 out of 3 replicates) were filtered for further analysis. After filtration, 1324 proteins/peptides were identified and tabulated. The proteins were classified based on their biological process in gene ontology using a PANTHER classification system as shown in FIG. 11B. Based on gene ontology, 9.3% of proteins were classified as either secreted by cell or as proteins involved in signal transduction. Furthermore, the proteins were classified by functional type as shown in FIG. 11C. Data indicated that 7% (Signal molecules/Extracellular matrix proteins/Cell adhesion proteins/Transporters) of the identified peptides have potential signaling function. Data was further evaluated using web-based bioinformatics tools such as SignalP and DeepLoc to identify signal peptides and to identify subcellular localization of proteins. SignalP predicted 123 (9.3%) proteins as having signal peptide domain, and DeepLoc predicted 63 (4.7%) proteins localized in the extracellular region. Skeletal muscle regeneration has three critical events that occur synergistically: 1) Myofiber formation, 2) Nerve reinnervation and 3) Angiogenesis. Therefore, proteins identified from the web-based bioinformatics tools were manually annotated, classified, and tabulated into proteins that affect myoblast behavior (Table 1), angiogenesis (Table 2), and nerve function (Table 3). Further, proteins with overlapping functions were elucidated and classified as shown in the Venn-diagram in FIG. 12. FIG. 12 illustrates a Venn-diagram illustrating the interactions of proteins annotated with roles in muscle, nerves and angiogenesis. Four specific proteins. Galectin-1, Progranulin, Cathepsin B. and Glypican-1, were identified to have a dual role in muscle repair and angiogenesis. Additionally, Prosaposin and Progranulin were identified to have roles in muscle repair and nerve function. Interestingly. Progranulin was identified to have a common role in muscle repair, nerve function, and angiogenesis. Based on the annotations, four proteins were identified to have a dual role in muscle repair and angiogenesis: Galectin-1, Progranulin. CathepsinB and Glypican-1. Additionally. Prosaposin and Progranulin were identified to have roles in muscle repair and nerve function. Interestingly, Progranulin, was identified to have a role in muscle repair, angiogenesis, and nerve function.

TABLE 1

List of proteins with function in muscle.

| S. No | Protein Name | Function | MS/MS Average | Reference |
|---|---|---|---|---|
| 1 | Prosaposin | Promotes myoblast fusion and attenuates loss of muscle mass after nerve injury | 76.7 | (Rende et al. 2001) |
| 2 | Galectin-1 | Skeletal muscle regeneration and myoblast differentiation | 76.0 | (Van Ry et al. 2015) |
| 3 | Chromogranin A | Deficiency renders muscle function and regeneration | 66.7 | (Tang et al. 2017) |
| 4 | Cathepsin B | Fusion of Myoblast during myogenesis | 33.7 | (Jane et al. 2002) |
| 5 | SPARC | Myoblast regeneration, Inhibits myoblast differentiation, Role in muscle function | 33.3 | (Jorgensen et al. 2017; Petersson et al. 2013) |
| 6 | Gelsolin | Regulates YAP-mediated mechanotransduction in skeletal muscle | 30.7 | (Fischer et al. 2016) |
| 7 | Insulin-like Growth Factor Binding Protein-6 | Regulates skeletal muscle differentiation | 24.7 | (Aboalola and Han 2017) |
| 8 | Progranulin | Regulates muscle growth, Regulates muscle hypertrophy | 24.0 | (Hu et al. 2012; Li et al. 2013) |
| 9 | Protein Kinase C | Myoblast fusion | 16.3 | (Madaro et al. 2011) |
| 10 | Glypican-1 | Myoblast migration | 16.0 | (Gutiérrez et al. 2014) |
| 11 | Dystroglycan 1 | Myotubes and muscle cell viability | 13.7 | (Montanaro et al. 1999) |
| 12 | Mac-2 Binding Protein | Regulates cell-cell interaction and muscle function through Galectin-3 | 13.3 | (Inohara et al. 1996) |
| 13 | Glucosamine-6-sulfatase | Regulates myoblast behavior through Heparin Sulfate | 8.3 | (Ghadiali et al. 2017) |

TABLE 2

List of proteins with function in angiogenesis.

| S. No | Protein Name | Function | MS/MS Average | Reference |
|---|---|---|---|---|
| 1 | Galectin-1 | Angiogenesis | 76.0 | (Thijssen and Griffioen 2014) |
| 2 | Secretogranin III | Angiogenesis | 37.7 | (Tang et al. 2018) |
| 3 | Hepatoma-derived Growth Factor | Angiogenesis | 34.0 | (Ojima et al. 2014) |
| 4 | Cathepsin B | Neovascularization and angiogenesis | 33.7 | (Im et al. 2005) |
| 5 | Tissue Plasminogen Activator | Angiogenesis | 29.7 | (Yip et al. 2013) |
| 6 | Progranulin | Angiogenesis | 24.0 | (Eguchi et al. 2017) |
| 7 | Peroxidoxin | Angiogenesis | 18.0 | (Riddell et al. 2012) |
| 8 | Placenta Growth Factor | Angiogenesis and proangiogenesis | 17.3 | (Zimna et al. 2018) |
| 9 | Protein Kinase C | Angiogenesis | 16.3 | (Xu et al. 2008) |
| 10 | Glypican-1 | Angiogenesis | 16.0 | (Aikawa et al. 2008) |
| 11 | Follistatin-related Protein 1 | Revascularization | 8.7 | (Ouchi et al. 2008) |
| 12 | Cystatin C | Angiogenesis | 7.7 | (Zou et al. 2017) |
| 13 | Neuropilin-1 | Angiogenesis | 4.3 | (Kawamura et al. 2008) |
| 14 | Prorlycarboxypeptidase | Promotes angiogenesis and vascular repair | 4.0 | (Adams et al. 2013) |

TABLE 3

List of proteins with function in nerve.

| S. No | Protein Name | Function | MS/MS average | Reference |
|---|---|---|---|---|
| 1 | Secretogranin II | Neuronal differentiation | 424.0 | (Li et al. 2008) |
| 2 | Neurosecretory Protein VGF | Neurite outgrowth and neuroprotection | 129.3 | (Takeuchi et al. 2018) |
| 3 | Calreticulin | Schwann cell migration and proliferation | 84.3 | (Huang et al. 2016) |
| 4 | Prosaposin | Neurotrophic factor, Neurite outgrowth | 76.7 | (O'Brien et al. 1994) |
| 5 | Amyloid Precursor Protein | Neuromuscular junction formation | 46.3 | (Stanga et al. 2016) |
| 6 | Calsyntenin-1 | Axon development | 25.3 | (Lee et al. 2017) |
| 7 | Progranulin | Neurite outgrowth and survival | 24.0 | (Van Damme et al. 2008) |
| 8 | Calcium-binding Protein 1 | Regulates calcium channels, which in turn regulates neurite outgrowth | 16.7 | (Yang et al. 2018) |
| 9 | Gicerin | Neurite outgrowth | 11.7 | (Taira et al. 1998) |
| 10 | Tenascin-R | Neurogenesis | 7.7 | (Xu et al. 2014) |
| 11 | Basigin | Neurite outgrowth | 7.7 | (Mitsumoto et al. 2001) |
| 12 | Armet Protein | Neurite outgrowth | 6.3 | (Tseng et al. 2017) |
| 13 | Cysteine and Glycine-rich Protein 1 | Dendrite growth | 4.3 | (Ma et al. 2011) |
| 14 | Metalloproteinase inhibitor 2 | Neuronal differentiation | 2.7 | (Pérez-Martínez and Jaworski 2005) |
| 15 | Neudesin | Neural cell proliferation and differentiation | 2.7 | (Kimura et al. 2006) |

DISCUSSION

Myoblast survival and proliferation are critical cellular processes that affect the efficacy of in situ skeletal muscle regeneration. Previous studies have shown that promoting myoblast proliferation and survival while delaying the cell cycle withdrawal for differentiation present favorable conditions for in vivo skeletal muscle repair. Thus, identifying bioactive factors that facilitate myoblast survival and proliferation represents a promising approach for successful biomaterials-based skeletal muscle regeneration. Recently, there has been a growing interest to harness cell-secreted biological factors in the form of secretome for regenerative applications. Secretome offers a potent combination of signaling molecules, growth factors, extracellular matrix proteins and enzymes that modulate cell-cell and cell-material interactions. In this study, we have demonstrated for the first time the important role of nerve cell secretome in modulating myoblast survival, proliferation, and differentiation in both 2D and 3D cultures.

Cell-cell communication is an orchestrated process tightly governed by 3D ECM and cell-secreted factors involved in autocrine and paracrine signaling functions. Accordingly, we have previously developed an aligned polymeric fiber scaffold system that mimics the native microenvironment of skeletal muscle ECM by electrospinning. By optimizing the scaffold fiber topography and mechanical properties, we have demonstrated that aligned PLGA 85:15 electrospun fibers facilitate favorable contact guidance and cell-material interactions for myoblast proliferation and differentiation. Using this optimized 3D fiber scaffold system, we have shown that PC12-secreted signaling factors, which regulated myoblast proliferation, survival, and differentiation in vitro in a dose-dependent manner, thereby corroborating our findings with 2D TCPS culture. For example, higher secretome concentration derived from 5M cells resulted in a 12-fold and 5-fold increase in cell numbers after 5 days of culture as compared to SF controls for 2D and 3D cultures, respectively. Interestingly, higher secretome concentration led to reduced myoblast differentiation as evidenced from expression of myogenic markers such as MyoG and MYH8, which suggested delayed withdrawal from the cell cycle. Similar to the results observed in our study, it has been shown that MSCs secrete signaling factors modulated proliferation of myoblasts. Furthermore. El-Habta et al. demonstrated that adipose-derived stem cells differentiated through Schwann cell lineage secrete acetyl choline, a signaling molecule that modulates proliferation of myoblasts in vitro and in vivo.

In an effort to develop biomaterial-based cellular matrix system capitalizing the biological benefits of PC12-derived secretome on myoblast performance, we designed and synthesized a biomimetic, tunable HCP hydrogel system comprised of thiolated HA and CS cross-linked with PEG through thiol-ene click chemistry. This hydrogel system offers an attractive 3D microenvironment that recapitulates the physical, chemical and biological properties of natural cell ECM (FIGS. 8A-D). For example, CS-based hydrogels have been reported to support self-renewal of neural stem cells and facilitate neurite outgrowth and delivery of neurotrophic signals. Variations in the cross-linking density allowed for modulating physical properties of hydrogels and cell-hydrogel interactions. Specifically, it has been reported that healthy, resting skeletal muscle has an average elastic modulus of 12±4 kPa. Accordingly, we have optimized the HCP hydrogel to process a storage modulus G' of 13.0 t 1.8 kPa, which is within the optimal range for applications in skeletal muscle regeneration. Furthermore, the HCP hydrogel has a well-defined, interconnected, microporous structure that is desirable for diffusion of cell secreted factors. Our in vitro studies with PC12 cells demonstrated the ability of the hydrogel to support 3D cell encapsulation and proliferation with high viability, thereby establishing the HCP culture system as a suitable cell matrix to evaluate the effects of the signaling factors secreted by PC12 cells on myoblasts in a co-culture system.

Transwell co-culture provides a unique platform to evaluate in situ effects of PC12 secretome on C2C12 cells. In our experiments. C2C12 cells were seeded on the well bottom and HCP hydrogels encapsulating PC12 cells placed within a permeable insert. To ensure comparable cell number to culture media volume ratios with 2D and 3D cultures using secretome obtained from 5M cells, we selected three PC12 densities per hydrogel: 200 k, 500 k and 1M cells. Interestingly, HCP hydrogels encapsulating PC12 significantly increased proliferation with reduced myogenic differentiation, which was presumably due to secretome factors released by encapsulated PC12 cells. This suggested that the biological benefits of PC12 secretome could be realized by utilizing HCP hydrogel-based cell-encapsulation approaches.

To further understand molecular mechanisms governing the PC12 secretome on myoblasts, proteomic studies were performed to characterize, analyze and identify potential target proteins and peptides in the secretome. Various signaling molecules and proteins secreted by nerve cells have diverse function in nerve cells themselves, on other cell types and in tissue regeneration. The major challenge in analyzing the secretome's proteomics involves distinguishing the proteins actually secreted from the cells from the artifacts. To eliminate this complexity in analysis, secretome was collected and analyzed in SF media. We have characterized and analyzed a total of 2088 protein/peptides identified from the secretome through label free LC/MS/MS technique. The entire secretome contains proteins that have intracellular domains and functions along with secreted proteins. This could be due to cell death and leakage, or these proteins might have non-classical pathways through which they get released. Notably, we have annotated several proteins that have overlapping functions in muscle repair, nerve innervation, and angiogenesis. For example, Galectin-1 has been reported to be a potential therapeutic to improve muscle function in muscle disorders. Furthermore, prosaposin-based peptides have been shown to have therapeutic potential in nerve disorders. Similarly, progranulin has been demonstrated to have therapeutic efficacy to treat neurodegenerative disorders and wound healing. Our ongoing work is focused on molecular signaling studies of these proteins which will provide further insights into identification of potential therapeutic targets and development of advanced biomaterials for accelerated skeletal muscle regeneration. Conclusions.

In the present study, we studied the effects of factors secreted by P12 cells on myoblasts in vitro, and further developed a mechanically suitable HCP hydrogel via thiol-ene click chemistry to combine hyaluronic acid (HA), chondroitin sulphate (CS), and polyethylene glycol (PEG) as a cellular matrix encapsulating PC12 cells to modulate myoblast function. It is hypothesized that the factors secreted by P12 cells can be optimized to enhance nerve-muscle cell interactions and myoblast performance. The combination of HA and CS would offer an extracellular matrix (ECM)-mimicking microenvironment whereas the selection of PEG as a crosslinker is based on its established biocompatibility and chemical versatility. Both tissue culture polystyrene (TCPS) and 3D aligned electrospun fibers made from poly (lactide-co-glycolide) (PLGA 85:15) mimicking anisotropic organization of skeletal muscles were used as myoblast culture substrates to study nerve-secreted factors collected in the form of secretome on myoblast behavior involving cell survival, proliferation, and differentiation. Furthermore, we evaluated myoblast responses when co-cultured with HCP hydrogels encapsulating PC12 cells secreting signaling factors. Additionally, we analyzed the secretome profile to identify and examine nerve-secreted proteins that could potentially modulate skeletal muscle regeneration.

Nerve cells secrete neurotrophic factors that play a critical role in neuronal survival, proliferation and regeneration. However, their role in regulating myoblast behavior and skeletal muscle repair remains largely unexplored. Our in vitro studies have elucidated the role of PC12 secretome on myoblasts on both 2D TCPS and 3D aligned fiber scaffolds involving survival, proliferation, and differentiation. We have engineered a mechanically appropriate HCP hydrogel system for PC12 encapsulation and 3D culture, and further demonstrated the feasibility of utilizing such an optimized HCP hydrogel system to encapsulate PC12 cells and enhance myoblast proliferation by recapitulating the effects of PC12 secretome on myoblasts in a co-culture model. Additionally, proteomics analysis with the PC12-derived secretome has revealed the biological role and overlapping functions of nerve-secreted proteins for skeletal muscle regeneration involving myoblast behavior, nerve function, and angiogenesis. These experiments provide insights into the nerve-muscle interactions and pave the way for developing advanced biomaterials strategies incorporating nerve cell secretome for accelerated skeletal muscle regeneration. Supplemental Information.

Inmmunofluorescent staining and qPCR: For immunofluorescent staining, the cells were fixed in 4% paraformaldehyde (in PBS) for 10 minutes. The cells were then incubated in 100 mM glycine for 10 minutes and washed with PBS three times. Next, the cells were incubated in blocking buffer (2% Bovine serum albumin, 5% Goat serum, 0.01% Triton X100 and 0.01% Sodium azide) for at least 1 h. Afterwards, the samples were incubated in MF-20 antibody (Developmental Studies Hybridoma Bank; 1:50) overnight at 4° C. The samples were subsequently washed thrice in PBS before incubating in anti-mouse secondary antibody for 1 h. Finally, the cells were counterstained for nucleus with Hoechst 33342.

For qPCR studies, total RNA was extracted using Trizol reagent according to manufacturer's instructions. Total RNA was reverse transcribed to cDNA using reverse primers and M-MLV reverse transcriptase (Invitrogen). The qPCR was performed with a Roche light cycler instrument using SYBR green master mix. Details about the primers used in the study in given in Table 4.

TABLE 4

List of primers.

| Gene Name | Primer Sequence (5'-3') |
|---|---|
| 18s | F: AGT CCC TGC CCT TTG TAC ACA (SEQ ID NO: 1) |
|  | R: CGA TCC GAG GGC CTC ACT A (SEQ ID NO: 2) |
| MyoD | F: GGC TAC GAC ACC GCC TAC TA (SEQ ID NO: 3) |
|  | R: CGA CTC TGG TGG TGC ATC TG (SEQ ID NO: 4) |
| MyoG | F: TGC CCA GTG AAT GCA ACT CC (SEQ ID NO: 5) |
|  | R: TTG GGC ATG GTT TCG TCT GG (SEQ ID NO: 6) |
| MYH8 | F: GGA GAG GAT TGA GGC CCA AAA (SEQ ID NO: 7) |
|  | R: CAC GGT CAC TTT CCC TCC ATC (SEQ ID NO: 8) |

Aligned electrospun fiber fabrication: Poly(lactide-co-glycolide) (PLGA 85:15) with a molecular weight—150 kDa was used for this study. To form electrospun fibers, 7% PLGA solution in Tetrahydrofuran (THF): N, N-Dimethylformamide (DMF) (3:1) was loaded into a 10 mL syringe attached to an 18 G blunt needle. The polymer solution was fed at a rate of 2 mL/h while the needle was connected to a 20 kV power supply. The collector was placed 20 cm away from the needle. To obtain aligned electrospun fibers, a custom drum collector was employed as reported in our previous study. The drum collector was rotated at a speed of 1000 rpm. Fiber mats were allowed to dry overnight after 5 h of continuous electrospinning. The mats were then stored in dehumidifier until further use.

Myoblast culture with aligned electrospun fibers: To begin, 8 mm diameter circular discs were cut out of the electrospun fiber mats and UV-sterilized inside a chamber for a minimum of 15 minutes on each side. Then, the discs were placed in a 24-well plate and incubated in C2C12 growth media overnight to allow better cell adhesion. C2C12 myoblasts were seeded at a density of $2\times10^4$ cells per scaffold for the proliferation studies and allowed to adhere overnight. The metabolic activity of cells at predetermined time points (Day 1, 3 and 5) as described above. For the differentiation studies, cells were seeded at a density of $2\times10^5$ cells per scaffold and allowed to adhere overnight. The cells were allowed to differentiate for 4 days and characterized with immunofluorescent staining and qPCR as mentioned before.

Proteomic sample preparation: To extract the proteins, the secretome was concentrated using a protein concentrator (Thermo Scientific, PES 10 kDa cutoff). The concentration of the proteins was evaluated using BCA assay (Pierce BCA assay kit. Thermo Fisher) as per manufacturer's instruction. The concentrated proteins (~100 µg) were precipitated using five times volume of ice-cold acetone (pre-incubated at −20° C.) and incubated overnight at −20° C. Protein pellets were collected by centrifugation at 14000×g for 15 minutes at 4° C. The pellets were resuspended in 10 µL of solution (10 mM DTT and 8M urea in 25 mM Ammonium bicarbonate) and incubated at 37° C. for 1 hour to reduce disulfide bonds. Then, 10 µL of alkylating agent (97.5% Acetonitrile (ACN), 2% Iodoethanol and 0.5% Triethyl Phosphate) was added and incubation allowed to proceed for another 1 hour at 37° C. Next, the samples were then vacuum-dried to remove the solvent, after which 80 µL of Lys-C/Trypsin mixture (0.05 µg/µL) was added to the dried pellet. Next, the samples were transferred to a barocycler and digested at high pressure (50° C.; 50 seconds at 20 kpsi, 10 seconds at atmospheric pressure for a total of 120 cycles over 2 hours). Then, the digested samples were desalted by passing through a C18 column (UltraMicro Spin Column Kit. The Nest Group, Inc.) as per the manufacturer's instructions. The cleaned peptides were vacuum-dried and resuspended in solution consisting of 3% ACN, 0.1% formic acid in water. Peptide concentration was estimated using BCA assay, and the samples were diluted to obtain a concentration of 0.5 µg/L. For the LC/MS/MS analysis, 2 µL (1 µg) of the peptide solution was loaded into the trap column. Samples were analyzed by a reverse phase HPLC-ESI/MS/MS system using a Dionex UltiMate 3000 RSLC nano System (Thermo Fisher Scientific. Odense. Denmark) coupled to a Q-Exactive High Field (HF) Hybrid Quadrupole Orbitrap MS and a Nano-electrospray Flex ion source (Thermo Fisher Scientific). The LC-MS/MS data was analyzed using MaxQuant for protein identification and label-free quantitation. Analysis was performed for both 1M and 5M groups, however data analysis for 5M is only reported.

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present invention. Thus, it should be understood that although the present invention has been specifically disclosed by specific embodiments and optional features, modification and variation of the concepts herein disclosed may be resorted to by those of ordinary skill in the art, and that such modifications and variations are considered to be within the scope of embodiments of the present invention.

Exemplary Embodiments

The following exemplary embodiments are provided, the numbering of which is not to be construed as designating levels of importance:

Embodiment 1 provides a composition for regeneration of skeletal muscle, the composition comprising:
a nerve cell secretome or an isolate thereof.

Embodiment 2 provides the composition of Embodiment 1, wherein the nerve cell secretome or the isolate thereof comprises one or more signaling factors that are effective to modulate skeletal muscle cell behavior.

Embodiment 3 provides the composition of any one of Embodiments 1-2, wherein the nerve cell secretome or the isolate thereof is effective to promote regeneration of skeletal muscle, promote innervation of skeletal muscle, or a combination thereof.

Embodiment 4 provides the composition of any one of Embodiments 1-3, wherein the nerve cell secretome or the isolate thereof is effective to promote survival and proliferation of myoblasts and/or myogenic cells, promote myofiber formation, promote muscle innervation, promote angiogenesis, or a combination thereof.

Embodiment 5 provides the composition of any one of Embodiments 1-4, wherein the nerve cell secretome comprises Galectin-1, Progranulin. CathepsinB, Glypican-1, Prosaposin. or a combination thereof.

Embodiment 6 provides the composition of any one of Embodiments 1-5, wherein the composition comprises the isolate of the nerve cell secretome.

Embodiment 7 provides the composition of Embodiment 6, wherein the isolate of the nerve cell secretome comprises Galectin-1. Progranulin, CathepsinB. Glypican-1, Prosaposin, or a combination thereof.

Embodiment 8 provides the composition of any one of Embodiments 1-7, wherein the nerve cells comprise a unipolar nerve cell, a biopolar nerve cell, a multipolar nerve cell, an anaxonic nerve cell, a psudounipolar nerve cell, a basket nerve cell, a Betz nerve cell, a Lugaro nerve cell, a medium spiny nerve cell, a Purkinje nerve cell, a Renshaw nerve cell, a unipolar brush nerve cell, a granule nerve cell, an anterior horn nerve cell, a spindle nerve cell, an afferent nerve cell, an efferent nerve cell, an interneuron nerve cell, a cholinergic nerve cell, an adrenergic nerve cell, a GABAergic nerve cell, a glutamatergic nerve cell, a dopaminergic nerve cell, a serotonergic nerve cell, a purinergic nerve cell, a histaminergic nerve cell, a catecholamine nerve cell, or a combination thereof.

Embodiment 9 provides the composition of any one of Embodiments 1-8, wherein the nerve cells comprise a catecholamine nerve cell.

Embodiment 10 provides the composition of any one of Embodiments 1-9, wherein the nerve cells comprise an adrenal pheochromocytoma (PC12) cell line.

Embodiment 11 provides the composition of any one of Embodiments 1-10, wherein the nerve cell secretome is a secretome from a culture of the nerve cells having a concentration of the nerve cells in culture media of $1\times10^3$ to $1\times10^{10}$ nerve cells per 10 mL of the culture media.

Embodiment 12 provides the composition of any one of Embodiments 1-11, wherein the nerve cell secretome is a secretome from a culture of the nerve cells having a concentration of the nerve cells in culture media of $1\times10^4$ to $1\times10^7$ of the nerve cells per 10 mL of the culture media.

Embodiment 13 provides the composition of any one of Embodiments 1-12, wherein the nerve cell secretome is a secretome from a culture of the nerve cells having a concentration of the nerve cells in culture media of $3\times10^5$ to $5\times10^6$ of the nerve cells per 10 mL of the culture media.

Embodiment 14 provides the composition of any one of Embodiments 1-13, wherein the nerve cell secretome is a secretome from a culture of the nerve cells having a concentration of the nerve cells in culture media of $1\times10^3$ to $9\times10^6$ of the nerve cells per 10 mL of the culture media.

Embodiment 15 provides the composition of any one of Embodiments 1-14, wherein the nerve cell secretome is a secretome from a culture of the nerve cells having a concentration of the nerve cells in culture media of $5\times10^5$ to $4\times10^6$ of the nerve cells per 10 mL of the culture media.

Embodiment 16 provides the composition of any one of Embodiments 1-15, wherein the nerve cell secretome is a secretome from a culture of the nerve cells having a concentration of the nerve cells in culture media of $2\times10^6$ to $1\times10^7$ of the nerve cells per 10 mL of the culture media.

Embodiment 17 provides the composition of any one of Embodiments 1-16, wherein the composition is an injectable composition.

Embodiment 18 provides a medical implant comprising the composition of any one of Embodiments 1-17.

Embodiment 19 provides the medical implant of Embodiment 18, wherein the medical implant further comprises a fiber scaffold.

Embodiment 20 provides the medical implant of Embodiment 19, wherein the fiber scaffold comprises a polymeric fiber scaffold.

Embodiment 21 provides the medical implant of any one of Embodiments 19-20, wherein the fiber scaffold is an electrospun fiber scaffold.

Embodiment 22 provides the medical implant of any one of Embodiments 19-21, wherein the fiber scaffold comprises tissue culture polystyrene (TCPS), poly(lactide-co-glycolide), or a combination thereof.

Embodiment 23 provides the medical implant of any one of Embodiments 19-22, wherein the fiber scaffold mimics the native microenvironment of skeletal muscle.

Embodiment 24 provides the medical implant of any one of Embodiments 19-23, wherein the fiber scaffold comprises skeletal muscle myoblasts and/or myogenic cells.

Embodiment 25 provides the medical implant of Embodiment 24, wherein at least some of the skeletal muscle myoblasts and/or myogenic cells are added to and/or cultured on the fiber scaffold prior to implantation of the medical implant.

Embodiment 26 provides an implantable therapeutic material for regeneration of skeletal muscle comprising:
a hydrogel; and
nerve cells encapsulated within the hydrogel, wherein at least some of the nerve cells are living.

Embodiment 27 provides the implantable therapeutic material of Embodiment 26, wherein the hydrogel is a 3D matrix that encapsulates the nerve cells.

Embodiment 28 provides the implantable therapeutic material of any one of Embodiments 26-27, wherein the nerve cells comprise a unipolar nerve cell, a biopolar nerve cell, a multipolar nerve cell, an anaxonic nerve cell, a psudounipolar nerve cell, a basket nerve cell, a Betz nerve cell, a Lugaro nerve cell, a medium spiny nerve cell, a Purkinje nerve cell, a Renshaw nerve cell, a unipolar brush nerve cell, a granule nerve cell, an anterior horn nerve cell, a spindle nerve cell, an afferent nerve cell, an efferent nerve cell, an interneuron nerve cell, a cholinergic nerve cell, an adrenergic nerve cell, a GABAergic nerve cell, a glutamatergic nerve cell, a dopaminergic nerve cell, a serotonergic nerve cell, a purinergic nerve cell, a histaminergic nerve cell, a catecholamine nerve cell, or a combination thereof.

Embodiment 29 provides the implantable therapeutic material of any one of Embodiments 26-28, wherein the nerve cells comprise a catecholamine nerve cell.

Embodiment 30 provides the implantable therapeutic material of any one of Embodiments 26-29, wherein the nerve cells comprise an adrenal pheochromocytoma (PC12) cell line.

Embodiment 31 provides the implantable therapeutic material of any one of Embodiments 26-30, wherein the nerve cells encapsulated within the hydrogel release a nerve cell secretome such that the hydrogel releases the secretome.

Embodiment 32 provides the implantable therapeutic material of Embodiment 31, wherein the secretome comprises Galectin-1, Progranulin. CathepsinB, Glypican-1, Prosaposin, or a combination thereof.

Embodiment 33 provides the implantable therapeutic material of any one of Embodiments 26-32, wherein the hydrogel is a reaction product of polyvinyl alcohol, polyethylene glycol, sodium polyacrylate, an acrylate polymer, an acrylate copolymer, polylactic acid, a polylactic acid copolymer, polyglycolic acid, a polyglycolic acid copolymer, poly(lactic-co-glycolic acid), poly(amino acids), polyphosphazenes, poly(phosphoesters), collagen, gelatin, fibrin, agarose, chitosan, cellulose, a cellulose derivative, methylcellulose, hyaluronan, elastin, dextran, chondroitin sulfate, agarose, alginate, heparin, an elastin-like-polypeptide (ELP), or a combination thereof.

Embodiment 34 provides the implantable therapeutic material of any one of Embodiments 26-33, wherein the hydrogel is a reaction product of hyaluronic acid, chondroitin sulfate, polyethylene glycol or a copolymer thereof, or a combination thereof.

Embodiment 35 provides the implantable therapeutic material of any one of Embodiments 26-34, wherein the hydrogel is a reaction product of starting materials comprising hyaluronic acid, chondroitin sulfate, and polyethylene glycol.

Embodiment 36 provides the implantable therapeutic material of any one of Embodiments 26-35, wherein the hydrogel has a concentration of the nerve cells of 10,000 cells per 20 microliters of the hydrogel to 10,000,000 cells per 20 microliters of the hydrogel.

Embodiment 37 provides the implantable therapeutic material of any one of Embodiments 26-36, wherein the hydrogel has a concentration of the nerve cells of 100,000 cells per 20 microliters of the hydrogel to 2,000,000 cells per 20 microliters of the hydrogel.

Embodiment 38 provides the implantable therapeutic material of any one of Embodiments 26-37, wherein the hydrogel has a concentration of the nerve cells of 200,000 cells per 20 microliters of the hydrogel to 1,000,000 cells per 20 microliters of the hydrogel Embodiment 39 provides the implantable therapeutic material of any one of Embodiments 26-38, wherein the hydrogel has a storage modulus that is approximately the same as soft tissue.

Embodiment 40 provides the implantable therapeutic material of any one of Embodiments 26-39, wherein the hydrogel has a storage modulus of 10 kPa to 16 kPa.

Embodiment 41 provides the implantable therapeutic material of any one of Embodiments 26-40, wherein the hydrogel has a storage modulus of 12 kPa to 14 kPa.

Embodiment 42 provides the implantable therapeutic material of any one of Embodiments 26-41, wherein the hydrogel has a storage modulus of 12.5 kPa to 13.5 kPa.

Embodiment 43 provides the implantable therapeutic material of any one of Embodiments 26-42, wherein the hydrogel is injectable.

Embodiment 44 provides a medical implant comprising the implantable therapeutic material of any one of Embodiments 26-43.

Embodiment 45 provides the medical implant of Embodiment 44 further including a fiber scaffold in contact with the implantable therapeutic material.

Embodiment 46 provides the medical implant of Embodiment 45 wherein the fiber scaffold includes a polymeric fiber scaffold.

Embodiment 47 provides the medical implant of any one of Embodiments 45-46, wherein the fiber scaffold is an electrospun fiber scaffold.

Embodiment 48 provides the medical implant of any one of Embodiments 45-47, wherein the fiber scaffold includes tissue culture polystyrene (TCPS), poly(lactide-co-glycolide), or a combination thereof.

Embodiment 49 provides the medical implant of any one of Embodiments 45-48, wherein the fiber scaffold mimics the native microenvironment of skeletal muscle.

Embodiment 50 provides the medical implant of any one of Embodiments 45-49, wherein the fiber scaffold includes the skeletal muscle myoblasts and/or myogenic cells.

Embodiment 51 provides the medical implant of Embodiment 50, wherein at least some of the skeletal muscle myoblasts and/or myogenic cells are added to and/or cultured on the fiber scaffold prior to implantation of the medical implant.

Embodiment 52 provides a method of forming the implantable therapeutic material of any one of Embodiments 26-43, the method comprising:
  adding the nerve cells to a hydrogel precursor composition;
  forming the hydrogel from the hydrogel precursor composition to form the implantable therapeutic material.

Embodiment 53 provides the method of Embodiment 52, further comprising multiplying the nerve cells in the implantable therapeutic material.

Embodiment 54 provides a method of regenerating skeletal muscle, the method comprising:
  applying the composition of any one of Embodiments 1-17 adjacent to skeletal muscle myoblasts and/or myogenic cells to regenerate skeletal muscle therefrom.

Embodiment 55 provides the method of Embodiment 54, wherein the applying comprises injecting the composition into skeletal muscle or adjacent thereto, implanting an implant that releases the composition to the skeletal muscle myoblasts and/or myogenic cells, or a combination thereof.

Embodiment 56 provides the method of any one of Embodiments 54-55, wherein the applying comprises applying the composition of any one of Embodiments 1-17 adjacent to an implanted fiber scaffold.

Embodiment 57 provides the method of Embodiment 56, further comprising implanting the fiber scaffold.

Embodiment 58 provides the method of any one of Embodiments 56-57, wherein the fiber scaffold comprises a polymeric fiber scaffold.

Embodiment 59 provides the method of any one of Embodiments 56-58, wherein the fiber scaffold is an electrospun fiber scaffold.

Embodiment 60 provides the method of any one of Embodiments 56-59, wherein the fiber scaffold comprises tissue culture polystyrene (TCPS), poly(lactide-co-glycolide), or a combination thereof.

Embodiment 61 provides the method of any one of Embodiments 56-60, wherein the fiber scaffold mimics the native microenvironment of skeletal muscle.

Embodiment 62 provides the method of any one of Embodiments 56-61, wherein the fiber scaffold comprises the skeletal muscle myoblasts and/or myogenic cells.

Embodiment 63 provides the method of Embodiment 62, wherein at least some of the skeletal muscle myoblasts and/or myogenic cells are added to and/or cultured on the fiber scaffold prior to implantation of the medical implant.

Embodiment 64 provides a method of regenerating skeletal muscle, the method comprising:
implanting the medical implant of any one of Embodiments 18-25, the implantable material of any one of Embodiments 26-43, or the medical implant of any one of Embodiments 44-51 adjacent to skeletal muscle myoblasts and/or myogenic cells to regenerate skeletal muscle therefrom.

Embodiment 65 provides the method of Embodiment 64, wherein after the implanting, the implantable material or medical implant comprising the implantable material releases secretome from the nerve cells in the hydrogel which regenerate skeletal muscle from the myoblasts and/or myogenic cells.

Embodiment 66 provides the method of any one of Embodiments 64-65, wherein after the implanting, the nerve cells grow and propagate in the hydrogel.

Embodiment 67 provides the method of any one of Embodiments 64-66, wherein the implanting of the medical implant of any one of Embodiments 18-25, the implantable material of any one of Embodiments 26-43 or the medical implant of any one of Embodiments 44-51 is effective to promote regeneration of skeletal muscle, promote innervation of skeletal muscle, or a combination thereof.

Embodiment 68 provides the method of any one of Embodiments 64-67, wherein the implanting of the medical implant of any one of Embodiments 18-25, the implantable material of any one of Embodiments 26-43 or the medical implant of any one of Embodiments 44-51 is effective to promote survival and proliferation of myoblasts and/or myogenic cells, promote myofiber formation, promote muscle innervation, promote angiogenesis, or a combination thereof.

Embodiment 69 provides the composition, medical implant, implantable therapeutic material, or method of any one or any combination of Embodiments 1-68 optionally configured such that all elements or options recited are available to use or select from.

What is claimed is:

1. A medical implant comprising:
an implantable therapeutic material for regeneration of skeletal muscle comprising
a hydrogel comprising a reaction product of a composition comprising hyaluronic acid, chondroitin sulfate, and polyethylene glycol or a copolymer thereof, wherein the hydrogel is injectable and has a storage modulus of 10 kPa to 16 kPa, and
nerve cells encapsulated within the hydrogel, wherein at least some of the nerve cells are living; and
a fiber scaffold in contact with the implantable therapeutic material, wherein the fiber scaffold is an aligned electrospun fiber scaffold that is a fiber mat, and wherein the fiber scaffold comprises skeletal muscle myoblasts and/or myogenic cells.

2. The medical implant of claim 1, wherein the hydrogel is a 3D matrix that encapsulates the nerve cells.

3. The medical implant of claim 1, wherein the nerve cells comprise a unipolar nerve cell, a bipolar nerve cell, a multipolar nerve cell, an anaxonic nerve cell, a pseudounipolar nerve cell, a basket nerve cell, a Betz nerve cell, a Lugaro nerve cell, a medium spiny nerve cell, a Purkinje nerve cell, a Renshaw nerve cell, a unipolar brush nerve cell, a granule nerve cell, an anterior horn nerve cell, a spindle nerve cell, an afferent nerve cell, an efferent nerve cell, an interneuron nerve cell, a cholinergic nerve cell, an adrenergic nerve cell, a GABAergic nerve cell, a glutamatergic nerve cell, a dopaminergic nerve cell, a serotonergic nerve cell, a purinergic nerve cell, a histaminergic nerve cell, a catecholamine nerve cell, or a combination thereof.

4. The medical implant of claim 1, wherein the nerve cells comprise a catecholamine nerve cell.

5. The medical implant of claim 1, wherein the nerve cells comprise an adrenal pheochromocytoma PC12 cell line.

6. The medical implant of claim 1, wherein the nerve cells encapsulated within the hydrogel release a nerve cell secretome such that the hydrogel releases the secretome.

7. The medical implant of claim 6, wherein the secretome comprises Galectin-1, Progranulin, CathepsinB, Glypican-1, Prosaposin, or a combination thereof.

8. The medical implant of claim 1, wherein the composition comprising hyaluronic acid, chondroitin sulfate, and polyethylene glycol or a copolymer thereof further comprises polyvinyl alcohol, sodium polyacrylate, an acrylate polymer, an acrylate copolymer, polylactic acid, a polylactic acid copolymer, polyglycolic acid, a polyglycolic acid copolymer, poly(lactic-co-glycolic acid), poly(amino acids), polyphosphazenes, poly(phosphoesters), collagen, gelatin, fibrin, agarose, chitosan, cellulose, a cellulose derivative, methylcellulose, elastin, dextran, agarose, alginate, heparin, an elastin-like-polypeptide (ELP), or a combination thereof.

9. The medical implant of claim 1, wherein the hydrogel has a storage modulus of 11 kPa to 16 kPa.

10. The medical implant of claim 1, wherein the hydrogel has a storage modulus of 11.5 kPa to 16 kPa.

11. The medical implant of claim 1, wherein the fiber scaffold comprises polyester, poly(lactide-co-glycolide), or a combination thereof.

12. The medical implant of claim 1, wherein at least some of the skeletal muscle myoblasts and/or myogenic cells are added to and/or cultured on the fiber scaffold prior to implantation of the medical implant.

13. The medical implant of claim 1, wherein the aligned electrospun fiber scaffold is formed by a method comprising collecting electrospun fibers on a rotating drum.

14. The medical implant of claim 1, wherein the hydrogel comprises an interconnected, microporous structure.

15. A method of forming the medical implant of claim 1, the method comprising:
adding the nerve cells to a hydrogel precursor composition;
forming the hydrogel from the hydrogel precursor composition to form the implantable therapeutic material; and
contacting the implantable therapeutic material with a fiber scaffold comprising skeletal muscle myoblasts and/or myogenic cells to form the medical implant.

16. A method of regenerating skeletal muscle, the method comprising:
implanting the medical implant of claim 1 adjacent to skeletal muscle myoblasts and/or myogenic cells to regenerate skeletal muscle therefrom.

17. A method of regenerating skeletal muscle, the method comprising:
implanting a medical implant adjacent to skeletal muscle myoblasts and/or myogenic cells to regenerate skeletal muscle therefrom, the medical implant comprising
an implantable therapeutic material for the regeneration of skeletal muscle comprising a hydrogel and nerve cells encapsulated within the hydrogel, wherein at least some of the nerve cells are living, wherein the nerve cells encapsulated within the hydrogel release a nerve cell secretome such that the hydrogel releases the secretome, and wherein the hydrogel is injectable and has a storage modulus of 10 kPa to 16 kPa, and
a fiber scaffold in contact with the implantable therapeutic material, wherein the fiber scaffold is an aligned electrospun fiber scaffold that is a fiber mat.

* * * * *